(12) United States Patent
Liu

(10) Patent No.: US 8,551,507 B2
(45) Date of Patent: Oct. 8, 2013

(54) TERPENE GLYCOSIDES AND THEIR COMBINATIONS AS SOLUBILIZING AGENTS

(75) Inventor: Zhijun Liu, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 0 days.

(21) Appl. No.: 13/379,072

(22) PCT Filed: Jun. 24, 2010

(86) PCT No.: PCT/US2010/039799
§ 371 (c)(1),
(2), (4) Date: Jan. 25, 2012

(87) PCT Pub. No.: WO2010/151653
PCT Pub. Date: Dec. 29, 2010

(65) Prior Publication Data
US 2012/0121696 A1    May 17, 2012

Related U.S. Application Data

(60) Provisional application No. 61/219,973, filed on Jun. 24, 2009.

(51) Int. Cl.
*A61K 31/7048* (2006.01)
*A61K 31/337* (2006.01)
*A61K 31/7034* (2006.01)
*C07H 15/24* (2006.01)

(52) U.S. Cl.
USPC ............ 424/400; 424/777; 514/25; 514/449; 514/450

(58) Field of Classification Search
None
See application file for complete search history.

(56) References Cited

U.S. PATENT DOCUMENTS

| | | | |
|---|---|---|---|
| 4,943,579 A | 7/1990 | Vishnuvajjala et al. | 514/283 |
| 5,635,611 A | 6/1997 | Ishiguro et al. | 536/4.1 |
| 6,673,843 B2 | 1/2004 | Arbiser | 514/679 |
| 2002/0076426 A1 | 6/2002 | Zirnstein et al. | 424/401 |
| 2006/0003053 A1 | 1/2006 | Ekanayake et al. | 426/51 |
| 2007/0032438 A1 | 2/2007 | Hu et al. | 514/23 |
| 2008/0242691 A1 | 10/2008 | Nakazawa et al. | 514/283 |
| 2011/0195161 A1* | 8/2011 | Upreti et al. | 426/103 |

FOREIGN PATENT DOCUMENTS

| | | |
|---|---|---|
| JP | 58-101660 | 6/1983 |
| JP | 01-299235 | 4/1989 |
| JP | 2001-048727 | 2/2001 |
| JP | 2001048727 A * | 2/2001 |
| WO | WO / 2009 / 126950 | 10/2009 |

OTHER PUBLICATIONS

Takashi Tanaka, Maki Kataoka, Nagisa Tsuboi, and Isao Kouno. New Monoterpene Glycoside Esters and Phenolic Constituents of Paeoniae Radix, and Increase of Water Solubilty of Proanthocyanidins in the Presence of Paeoniflorin. Chem. Pharm. Bull 48(2), 2000, pp. 201-207.*

Anne Marie Fine, Oligomeric Proanthocyanidin Complexes: History, Structure, and Phytopharmaceutical Applications. Alternative Medicine Review, vol. 5 No. 2, 2000, pp. 144-151.*

AMA Drug Evaluations Annual, "Clofazimine [Lamprene]," pp. 1619-1620 (1993).

Eicher, T et al., "Azole," in *The Chemistry of Heterocycles: Structure, Reactions, Syntheses, and Applications*, Wiley-VCH. (2003).

Kimata, H. et al., "Interaction of Saponin of Bupleuri Radix with Ginseng Saponin: Solubilization of Saikosaponin-a with Chikusetsu-saponin V (=Ginsenoside-Ro)," Chem. Pharm. Bull. (Tokyo), vol. 33, pp. 2849-2853 (1985).

Lipinski, C.A., "Drug-like Properties and the Causes of Poor Solubility and Poor Permeability," J Pharm Tox Meth, vol. 44, pp. 235-249 (2000).

Lipinski, C., et al., "Experimental and Computational Approaches to Estimate Solubility and Permeability in Drug Discovery and Development Settings," Adv. Drug Deliv. Rev., vol. 23, iss. 1-3, pp. 3-25 (1997).

Material Safety Data Sheet, "Artemisinin".
Material Safety Data Sheet, "Podophyllotoxin".
Material Safety Data Sheet, "Silybin (Silibinin)".

Sasaki, Y. et al., "Solubilizing Properties of Glycyrrhizin and Its Derivatives: Solubilization of Saikosaponin-a, the Saponin of Bupleuri Radix," vol. 36, No. 9, pp. 3491-3495 (1988).

Tanaka, T. et al., "New Monoterpene Glycoside Esters and Penolic Constsituents of Paeoniae Radix, and lncreaase of Water Solubility of Proanthocyanidins in the presence of Paeoniflorin," Chem. Pharm. Bull., vol. 48, No. 2, pp. 201-207 (2000).

Tanaka, T. et al., "Relationship between Hydrophobicity and Structure of Hydrolyzable Tannins, and Association of Tannins with Crude Drug Constituents in Aqueous Solution," Chem. Pharm. Bull., vol. 45, No. 12, pp. 1891-1897 (1997).

Tanaka, T. et al., "Rubusoside (b-D-glucosyl ester of 13-O-b-D-glucosyl-steviol), a sweet principle of *Rubus chingii* Hu (Rosacease)," Agricultural and Biological Chemistry, vol. 45, No. 9, pp. 2165-2166 (1981).

The Merck Index, 12th Edition, Ed. S. Budavari et al., pp. 282-283 (Camptothecin); 287-288 (Capsaicin); 450 (Curcumin); 737 (Gallic Acid); 894-895 (Itraconazole); and 1428 (Rutin) (1996).

* cited by examiner

*Primary Examiner* — Frederick Krass
*Assistant Examiner* — Michael P Cohen
(74) *Attorney, Agent, or Firm* — John H. Runnels; Bonnie J. Davis

(57) ABSTRACT

Several terpene glycosides (e.g., mogroside V, paenoiflorin, geniposide, rubusoside, rebaudioside A, steviol monoside and stevioside) were discovered to enhance the solubility of a number of pharmaceutically and medicinally important compounds, including but not limited to, paclitaxel, camptothecin, curcumin, tanshinone IIA, capsaicin, cyclosporine, erythromycin, nystatin, itraconazole, celecoxib, clofazimine, digoxin, oleandrin, nifedipine, and amiodarone. The use of the diterpene glycoside rubusoside and monoterpene glycoside paenoiflorin increased solubility in all tested compounds. The terpene glycosides are a naturally occurring class of water solubility-enhancing compounds that are nontoxic and that will be useful as new complexing agents or excipients in the pharmaceutical, agricultural (e.g., solubilizing pesticides), cosmetic and food industries.

40 Claims, 21 Drawing Sheets

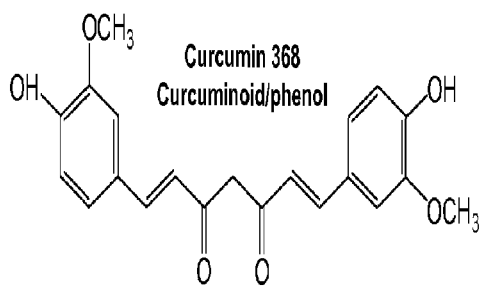
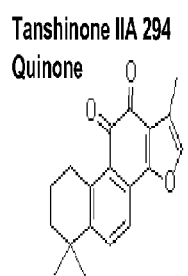
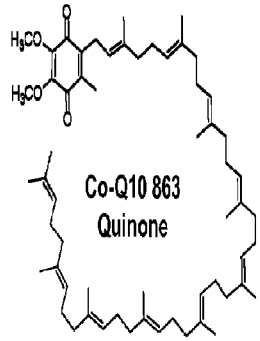
Fig. 1A
Fig. 1B
Fig. 1C
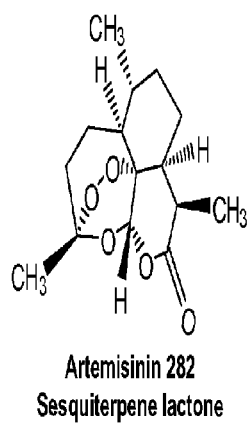
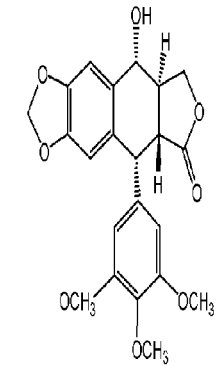
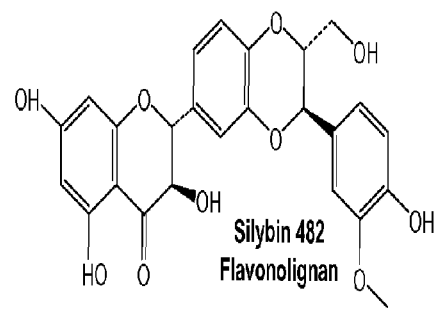
Fig. 1D
Fig. 1E
Fig. 1F
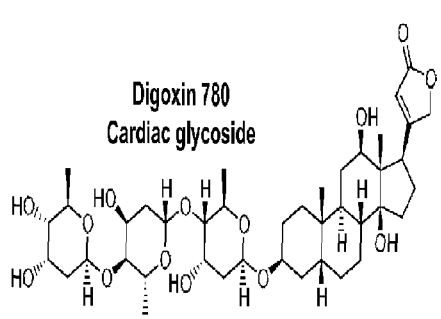
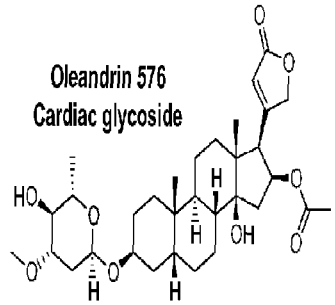
Fig. 1G
Fig. 1H Paeoliflorin Geniposide

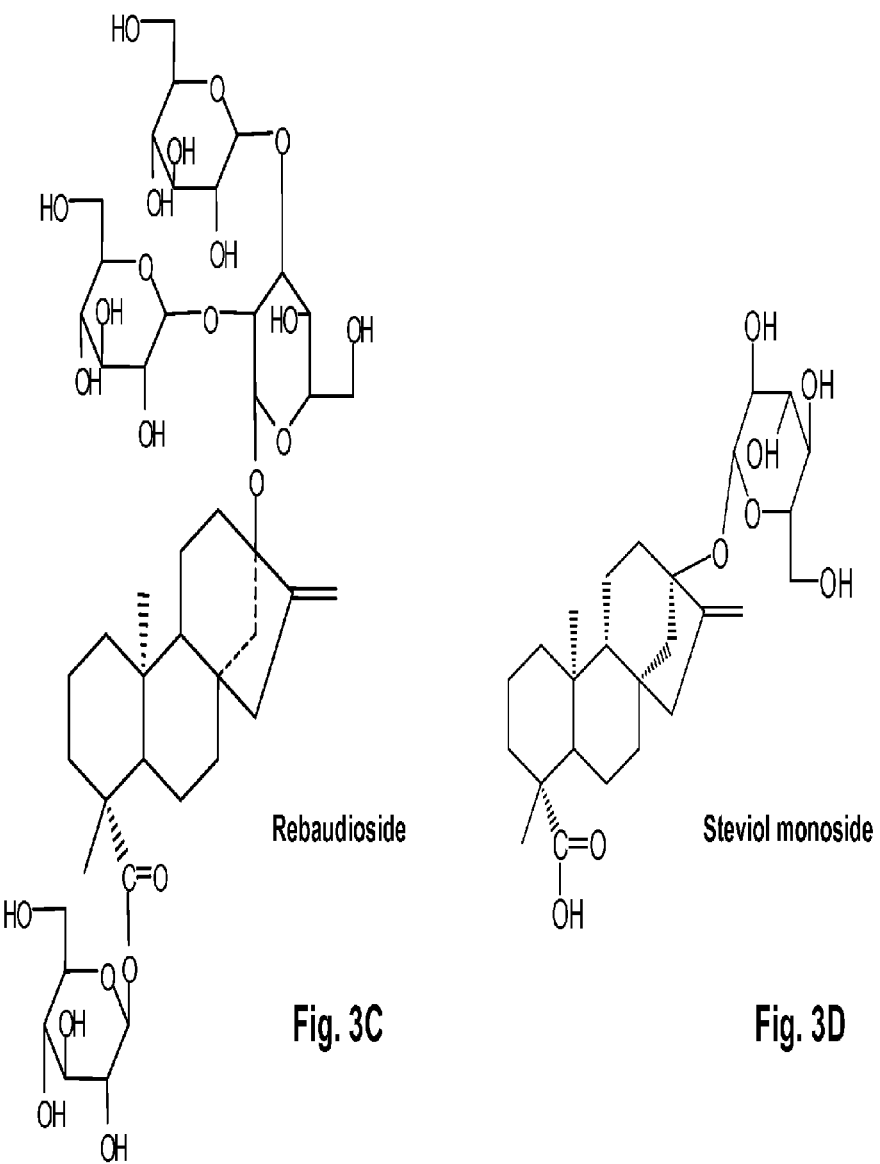
Fig. 3C Rebaudioside
Fig. 3D Steviol monoside

TERPENE GLYCOSIDES AND THEIR COMBINATIONS AS SOLUBILIZING AGENTS

This is the United States national stage of international application PCT/US2010/039799, international filing date Jun. 24, 2010, which claims the benefit of the Jun. 24, 2009 filing date of U.S. provisional patent application 61/219,973 under 35 U.S.C. §119(e).

TECHNICAL FIELD

This invention pertains to new compositions and uses for certain terpene glycosides as non-toxic, natural solubilizers for use in preparing aqueous solutions of various drugs, agricultural chemicals, cosmetics, and foods.

BACKGROUND ART

Drug Solubility and Complexing Agents

Poor aqueous solubility is a common obstacle to delivering pharmaceuticals or other bioactive compounds and is a major challenge in formulating new drug products. In a study of kinetic aqueous solubility of commercial drugs, 87% were found to have solubility in water of ≥65 µg/mL and 7%≤20 µg/mL (Lipinski, C., et al., Adv. Drug Deliv. Rev. (1997) 23:3-25). The minimum acceptable aqueous solubility for a drug is about 52 µg/mL solubility based on 1 mg/kg clinical dose and average permeability (C. A. Lipinski, J Pharm Tox Meth (2000) 44:235-249). The pharmaceutical industry has been employing various approaches to increasing water-insoluble drugs for pharmaceutical drug formulations. Commonly used approaches are the uses of one or more complexing agents (e.g., cyclodextrins), cosolvents (e.g., ethanol, polyethylene glycol), surfactants (e.g., Cremophor EL, Tween 80), emulsifiers (e.g., lecithin, glycerol), and liposome, micelle and nanosuspension techniques, alone or in combinations. Within this group, the use of complexing agents to improve solubility of water-insoluble drugs is increasing. Complexing agents improve water solubility by forming a non-covalent stoichiometric association with the pharmaceutical drug. Currently, the main complexing agents in the pharmaceutical industry are various forms of cyclodextrins ("CDs," molecular weight around 1135 Daltons), which form inclusion complexes with water-insoluble drug. The use of cyclodextrin inclusion complexation has successfully solubilized many insoluble drugs, including an antifungal, voriconazole, and an antipsychotic, ziprasidone mesylate, which use sulfobutylether-β-cyclodextrin as the complexing agent. The most important cyclodextrins are parent α-, β-, and γ-CD as well as two modified hydroxypropyl-β-CD and sulfobutylether-β-CD. However, even the use of cyclodextrins has its disadvantages. Some of these limitations include lack of compatibility of the drug molecules with the inclusion cavity of CDs, precipitation of the formed complexes of CD-drug during dilution (e.g., in the stomach), potential toxicity and quality control of uniform CDs, and low complexation efficiency for achieving desirable solubility effect. Therefore, new complexing agents that are superior to cyclodextrins in overcoming or reducing these limitations are needed for the formulations of pharmaceutical, cosmetic, agricultural chemicals, and foods products. Surfactant compounds are widely used in solubilizing pharmaceutical compounds because surfactants possess amphiphilic property and can form micelles or liposomes in water. The water-soluble micelles or liposomes have hydrophobic cores that can host water-insoluble molecules thus improve the solubility. Micelles can vary in sizes, some of which are nanosized, referred as nanomicelles. Surfactants are classified based on the charge of its hydrophilic groups: ionic (e.g., anionic, cationic) and non-ionic surfactants. Surfactants have many applications, for example, detergents, emulsifiers, cosmetics, and solubilizers. Some of the surfactants that are used for solubilizing water-insoluble drugs include propylene glycol, glycerol, sodium lauryl sulfate, and phospholipids. Micelles have many advantages in pharmaceutical formulation but solubilizing efficiency has been one of the major obstacles. New effective surfactants that are non-toxic natural ingredients and superior to the currently available surfactants hold promises of overcoming the limitations and advancing the formulations of pharmaceutical, cosmetic, agricultural chemicals, and foods products.

Important Compounds Insoluble in Water

Diterpenes.

Taxanes are diterpenes produced by the plants of the genus *Taxus* (yews) such as the Pacific Yew (*Taxus brevifolia*) in the family of Taxaceae. Taxanes include paclitaxel and docetaxel. Paclitaxel is the anti-cancer drug under the drug name of TAXOL® and docetaxel is used under the name of TAXOTERE® (Medicinal Natural Products—A Biosynthetic Approach, 1997, John Wiley & Sons, Chichester, England; pp 186-188) Paclitaxel is a known anti-cancer diterpenoid alkaloid and is not soluble in water. The structure of paclitaxel is shown in FIG. 1J. Therapeutic solutions of paclitaxel currently contain either oil or dehydrated alcohol or both; or paclitaxel is bound to albumin. None of these formulations are true water solutions. Other taxanes include baccatin III, 10-deacetylbaccatin III, cephalomannine, and 10-deacetylcephalomannine. These taxanes are characterized with a four-membered oxetane ring and a complex ester side-chain in their structures. All taxane compounds have poor water solubility. (U.S. Patent Application Publication no. 2007/0032438). Other medicinally important, but insoluble or poorly soluble diterpenes include retinoids (vitamin A, retinol (vitamin A1), dehydroretinol (vitamin A2), retinoic acid, 13-cis-retinoic acid and other retinol derivatives, ginkgolides and forsakolin (a promising drug for the treatment of glaucoma, congestive heart failure, and bronchial asthma).

Quinoline Alkaloids.

Quinoline alkaloids are alkaloids that possess quinoline in their structures and are terpenoid indole alkaloid modifications. Camptothecins isolated from the *Camptotheca acuminata* trees (Family Nyssaceae) are quinoline alkaloids. Camptothecin (CPT) is a cytotoxic alkaloid and is reported to have anti-tumor properties, perhaps by inhibiting topoisomerase 1. (See, for example, U.S. Pat. No. 4,943,579). The structure of camptothecin is shown in FIG. 1I. It has poor solubility in water (The Merck Index, 1996). Semi-synthetic analogues of camptothecins such as topotecan and irinotecan are approved chemotherapeutic drugs. Natural camptothecins include camptothecin, 10-hydroxycamptothecin, methoxycamptothecin, and 9-nitrocamptothecin. None of the natural camptothecins are water soluble (see, for example, U.S. Patent Application Publication no. 2008/0242691). Camptothecins have broad-spectrum anti-cancer activity, but poor water solubility has limited direct uses as chemotherapeutic agents. Other quinoline alkaloids include the long recognized anti-malarial drugs quinine, quinidine, cinchonidine, and cinchonine.

Curcuminoids/Phenols.

Curcuminoids/phenols are a class of compounds found in turmeric spice from the plant, *Curcuma longa*, of the ginger family. Curcuminoids include, for example, curcumin, desmethoxycurcumin, and bis-desmethoxycurcumin. Other phenols include, for example, tocopherol (vitamin E), propofol, and gingerols. Curcumin is an orange-yellow pigment that is found in the rhizome of *Curcuma longa*, the source of the spice turmeric. The structure of curcumin is shown in FIG. 1A. Curcumin has been reported to have several beneficial properties, including promotion of general health, anti-inflammatory and antimicrobial properties, and treatment for digestive disorders. (See, for example, U.S. Pat. No. 6,673, 843) Curcumin is a lipophilic compound that is insoluble in water (The Merck Index, 1996). Alpha-tocopherol, one of the most potent forms of Vitamin E, is a lipid-soluble phenol compound that is not soluble in water. Gingerols are lipid-soluble phenol compounds primarily isolated from the root of ginger (*Zingiber officinale*). Gingerols (e.g., 6-gingerol) may reduce nausea caused by motion sickness or pregnancy and may also relieve migraine.

Propofol is a drug for anesthetic and hypnotic uses. Currently, there are two drug forms using propofol. Its structure is shown in FIG. 1L. Propofol is formulated as an emulsion of a soybean oil/propofol mixture in water. Newer generic formulations contain sodium metabisulfite or benzyl alcohol. Propofol emulsion (also known as "milk of amnesia") is a highly opaque white fluid. The drug is sold as 200 mg propofol in 20 mL emulsifier (1%). The other drug form of propofol is a water-soluble form of the drug, fospropofol.

Quinones.

Quinones are a class of compounds having a fully conjugated cyclic dione structure. This class includes, for example, ubiquinones (coenzyme Q, such as coenzyme Q10), plastoquinones, anthraquinones (e.g., rhein, emodin, alizarin, and lucidin), phenanthraquinones (e.g., cryptotanshinone, tanshinone I, tanshinone IIA, and dihydrotanshinone), and di-anthraquinones (e.g., sennosides A and B). For example, tanshinone IIA is one of the natural analogues of tanshinone. The structure of tanshinone IIA is shown in FIG. 1B. Tanshinones have been reported to have various physiological activities from attenuating hypertrophy in cardiac myocytes to aiding in treatment of obesity. (See, for example, U.S. Patent Application Publication 2007/0248698). Tanshinone IIA (as well as other tanshinones such as tanshinone I) is soluble in methanol but insoluble in water.

Another quinone is coenzyme Q10 (often abbreviated as CoQ10), a benzoquinone. The structure of CoQ10 is shown in FIG. 1C. This oil-soluble vitamin-like substance is a component of an electron transport chain in aerobic cellular respiration. CoQ10 acts as an antioxidant and is often used as a dietary supplement. The problems with CoQ10 are its insolubility in water and low bioavailability. Several formulations have been developed and tested on animals or humans including attempts to reduce the particle size and increase surface area of the compound, soft-gel capsules with CoQ10 in oil suspension, the use of aqueous dispersion of solid CoQ10 with tyloxapol polymer, formulations based on various solubilizing agents, i.e. hydrogenated lecithin, and complexation with cyclodextrins, carriers like liposomes, nanoparticles, and dendrimers. Solubilizing CoQ10 in a water solution could have many uses as new medical treatments, including the administration by injection.

Microlides.

Microlides are a large family of compounds, many with antibiotic activity, characterized by a macrocyclic lactone ring typically 12-, 14-, or 16-membered (reflecting the number of units used), but can also be even larger polyene macrolides with microlide ring size ranging from 26 to 38-membered. Some examples of typical macrolides are erythromycins (14-membered) from *Streptomyces erythreus*, oleandomycin (14-membered) from *Streptomyces antibioticus*, spiramycin I, II, and III (16-membered) from *Streptomyces ambofaciens*, tylosin (16-membered) from *Streptomyces fradiae*, and avermectins (16-membered with a long polyketide chain). Some examples of polyene macrolides are amphotericin B from *Streptomyces nodosus*, nystatin from *Streptomyces noursei*, tacrolimus (23-membered) from *Streptomyces tsukubaensis*, and rapamycin (sirolimus; 31-membered).

Amphotericin B is a polyene antifungal, antibiotic from *Streptomyces* and has antimicrobial spectrum covering yeast and other fungi. It is a yellowish powder that is insoluble in water. The structure of amphotericin B is shown in FIG. 1K. Examples of applications of Amphotericin B: (1) antifungal: use of oral liposomal preparations of Amphotericin B to treat fungal disease, e.g., thrush; (2) use in tissue culture to prevent fungi from contaminating cell cultures. It is usually sold in a concentrated lipid complex/liposomal solution, either on its own or in combination with the antibiotics penicillin and streptomycin; (3) use as an antiprotozoal drug in otherwise untreatable parasitic protozoan infections such as visceral leishmaniasis and primary amoebic meningoencephalitis; and (4) use as an antibiotic in febrile, immunocompromised patients who do not respond to broad-spectrum antibiotics. An aqueous formulation of amphotericin would offer new ways to administer this important drug, including intravenous use.

Sesquiterpene Lactones.

Sesquiterpene lactones are a class of sesquiterpenes (15-carbon compounds) containing a lactone. Examples of insoluble sesquiterpenes are artemisinin (a new, highly-effective anti-malarial compound), dihydroartemissinin, and bilobalide (isolated from Ginkgo biloba).

Artemisinin is a sesquiterpene lactone drug used to treat multi-drug resistant strains of falciparum malaria. Artemisinin is isolated from the plant *Artemisia annua*, but can also be synthesized from artemisinic acid. Its structure is shown in FIG. 1D. Artemisinin is poorly soluble, which limits its bioavailability. Semi-synthetic derivatives of artemisinin, including artemether and artesunate, have been developed. However, their activity is not long-lasting, with significant decreases in effectiveness after one to two hours. To counter this drawback, artemisinin is given with lumefantrine (also known as benflumetol) to treat uncomplicated falciparum malaria. Lumefantrine has a half-life of about 3 to 6 days. Such a treatment is called ACT (artemisinin-based combination therapy); other examples are artemether-lumefantrine, artesunate-mefloquine, artesunate-amodiaquine, and artesunate-sulfadoxine/pyrimethamine. Recent trials have shown that ACT is more than 90% effective, with recovery from malaria after three days, even with chloroquine-resistant Plasmodium falciparum. A water solution of artemisinin would be highly desirable for direct parenteral applications.

Lignans.

Lignans are a class of compounds in which two phenylpropane coniferyl alcohol monomer units are coupled at the central carbon of the side-chain (lignans) or at another location (neolignans). Examples of lignans are podophyllotoxin (isolated from American Mayapple), 4'-demethylpodophyllotoxin, beta-peltatin, alpha-peltatin, desoxypodophyllotoxin, podophyllotoxone, matairesinol, yatein, and pinoresinol. Podophyllotoxin, also known as codylox or podofilox, is a lignan compound, and a non-alkaloid toxin isolated from the rhizome of American Mayapple (*Podophyllum peltatum*). Its structure is shown in FIG. 1E. Podophyllotoxin can also be synthesized biologically from two molecules of coniferyl alcohol. Podophyllotoxin is the pharmacological precursor for the important anti-cancer drug etoposide. It is also administered to treat genital warts. Podophyllotoxin is poorly soluble in water, and a water solution containing a pharmaceutically effective amount has not been available.

Flavonolignans.

Flavonolignans are a class of compounds structurally combined from flavonoid and lignan. These include compounds such as silybin, isosilybin, and silychristin (seen in the plant of milk thistle (*Silybum marianum*) from the family of Compositae. Silybin, also known as Silibinin, is the major active constituent of silymarin, the mixture of flavonolignans extracted from milk thistle (*Silybum marianum*). The structure of silybin is shown in FIG. 1F. Studies suggest that silybin has hepatoprotective (antihepatotoxic) properties and anti-cancer effects against human prostate adenocarcinoma cells, estrogen-dependent and estrogen-independent human breast carcinoma cells, human ectocervical carcinoma cells, human colon cancer cells, and both small and nonsmall human lung carcinoma cells. Poor water solubility and bioavailability of silymarin led to the development of enhanced formulations. Silipide (trade name SILIPHOS®), a complex of silymarin and phosphatidylcholine (lecithin), is about ten times more bioavailable than silymarin. It has been also reported that silymarin inclusion complex with β-cyclodextrin is much more soluble than silymarin itself. Glycosides of silybin show better water solubility and even stronger hepatoprotective effects. However, an aqueous solution of silybin in pharmaceutically acceptable amount, in its original and unmodified structure, has not been available for parenteral administrations.

Azole.

An azole is a class of five-membered nitrogen heterocyclic ring compounds containing at least one other noncarbon atom, for example, a nitrogen, sulfur or oxygen (Eicher, T.; Hauptmann, S. (2nd ed. 2003). The Chemistry of Heterocycles: Structure, Reactions, Syntheses, and Applications. Wiley-VCH. ISBN 3527307206). Itraconazole is a triazole with antifungal activities. Other triazole antifungal drugs include fluconazole, isavuconazole, voriconazole, pramiconazole, posaconazole, ravuconazole, fluconazole, fosfluconazole, epoxiconazole, triadimenol, propiconazole, metconazole, cyproconazole, tebuconazole, flusilazole and paclobutrazol. These compounds are practically insoluble in water (e.g., itraconazole, The Merck Index, 1996, p. 895). Itraconazole has relatively low bioavailability after oral administration.

Celecoxib is a pyrazole (a rare alkaloid), a compound that targets cyclooxygenase (COX) enzymes. The structure of celecoxib is shown in FIG. 1M. In medicine, pyrazoles are used for their analgesic, anti-inflammatory, antipyretic, antiarrhythmic, tranquilizing, muscle relaxing, psychoanaleptic, anticonvulsant, monoamineoxidase inhibiting, antidiabetic and antibacterial activities. Celecoxib is a COX-2 inhibitor. Celecoxib has poor solubility in water which reduces its bioavailability.

Cardiac Glycosides.

Cardiac glycosides are drugs used in the treatment of congestive heart failure and cardiac arrhythmia. The therapeutic functions, however, depend on the structure of the steroidal aglycone and the type and number of sugars attached. Based on the structure of aglycone, two types of cardiac glycosides are named: cardenolides (e.g., digoxin, oleandrin) and bufadienolides (e.g., hellebrigenin). The structure of digoxin is shown in FIG. 1G. Digoxin is used to treat congestive heart failure; the drug is formulated as an injection solution containing 40% propylene glycol and 10% alcohol to achieve 250 μg/mL concentration. Oleandrin may be used to treat congestive heart failure or cancer.

Dihydropyridine.

Dihydropyridines is a class of drugs as calcium channel blockers. Examples of dihydropyridine include nifedipine, amlodipine, aranidipine, azelnidipine, barnidipine, benidipine, cilnidipine, clevidipine, efonidipine, felodipine, isradipine, lacidipine, manidipine, lercanidipine, nicardipine, nilvadipine, nimodipine, nisoldipine, nitrendipine, and pranidipine. The structure of nifedipine is shown in FIG. 1O. Nifedipine is a calcium channel blocker drug, currently formulated in capsules. No injectable drugs are currently available.

Amiodarone.

Amiodarone is Class III agent (a potassium channel blocker) and an antiarrhythmic agent (medication used for irregular heart beat) used for various types of tachyarrhythmias (fast forms of irregular heart beat), both ventricular and supraventricular (atrial) arrhythmias. The structure of amiodarone is shown in FIG. 1P. Amiodarone is an antianginal and antiarrhythmic drug, currently available in oral and injection formulations.

Riminophenazine.

Riminophenazine is a class of fat soluble dyes used for the treatment of leprosy. It has been used investigationally in combination with other anti-mycobacterial drugs to treat Mycobacterium avium infections in AIDS patients. One example is clofazimine that has a marked anti-inflammatory effect and is given to control the leprosy reaction, erythema nodosum leprosum. (From AMA Drug Evaluations Annual, 1993, p1619). The structure of clofaximine is shown in FIG. 1N. Clofazimine is a non-steriodal, anti-inflammatory drug and is currently formulated using propylene glycol, oils, and beeswax.

Terpene Glycosides

Natural terpene glycosides are well known and exist in a variety of plant sources. They generally are terpene aglycons attached to at least one glucose, and the most common forms are diterpene glycosides and triterpene glycosides. Many of these compounds are known to be non-toxic and natural sweeteners. (U.S. Published Patent Application No. 2006/000305053). Rubusoside is a diterpene glycoside that is from Chinese sweet leaf tea leaves (*Rubus suavissimus*; Rosaceae). Rubusoside has a molecular formula C32H50O13 and molecular weight of 642.73. (From T. Tanaka et al., Rubusoside (b-D-glucosyl ester of 13-O-b-D-glucosyl-steviol), a sweet principle of *Rubus chingii* Hu (Rosacease), Agricultural and Biological Chemistry, vol. 45(9), pp. 2165-6, 1981). Rubusoside also has good solubility in water, alcohol and acetone ethyl acetate. It is a diterpene aglycone with two glucose molecules attached. (FIG. 3A) Diterpene glycosides have been shown by me to be good natural solubilizers. (International application no. PCT/US2008/040324; international publication no. WO 2009/126950). The entire contents of that published application is fully incorporated into this application. Another diterpene glycoside that is isolated from the Chinese sweet leaf tea (*Rubus suavissimus*; Rosaceae) is steviol monoside (FIG. 3D). The structure of steviol monoside has only one glucose molecule rather than two as in rubusoside. Steviol monoside can be isolated from the sweet leaf tea or be obtained through the acid hydrolysis of rubusoside to cleave one glucose molecules. Unlike rubusoside, steviol monoside is not a dominant diterpene glycoside in the sweet leaf tea plant.

Stevioside is a diterpene (steviol) glycoside that is isolated from the *Stevia* leaf (*Stevia rebaudiana*; Asteraceae). Stevioside has a molecular formula $C_{38}H_{60}O_{18}$ and a molecular weight of 804. The compound as shown in FIG. 3B is a diterpene aglycone with three glucose molecules. In pure form, it is a crystal or white powder. Another diterpene glycoside that is isolated from the *Stevia* leaf is rebaudioside A. The compound as shown in FIG. 3C is a diterpene aglycone with four glucose molecules. In pure form, it is a white powder.

Mogroside V is a triterpene glycoside that is isolated from the luohanguo fruit (*Siraitia grosvenorii*, formerly known as *Momordica grosvenori*; Curcubitaceae). The structure of mogroside V is shown in FIG. 2A. The sweet taste of luohanguo comes mainly from the mogrosides, a group of triterpene glycosides that make up approximately 1% of the flesh of the fresh fruit. Five different mogrosides are known, named with the numbers 1 to 5. The main mogroside in luohanguo is mogroside V. Mogroside V has a molecular formula $C_{60}H_{102}O_{29}$ and a molecular weight of 1286. A second triterpene glycoside is astragaloside IV with a structure as shown in FIG. 2B. One triterpene glycoside was reported to increase the solubility of saikpsaponin A. See H. Kimata et al., Chem. Pharm. Bull. (Tokyo), vol. 33:2849-2853, 1985; and Y. Sasaki et al., Chem. Pharm. Bull. (Tokyo), vol. 36:3491-3495 (1988).

Monoglycosides are also known. Two monoglycosides are paenoiflorin and geniposide. The structures of these two compounds are shown in FIGS. 2C and 2D, respectively. Paeoniflorin has been reported to increase the solubility of polymeric proanthocyanidins. Both were found in the extract from Paeonine Radix (Shaoyao), an important drug in Japanese and Chinese traditional medicine. See, for example, T. Tanaka et al., Chem. Pharm. Bull., vol. 48(2): 201-207, 2000; and T. Tanaka et al., Chem. Pharm. Bull., vol. 45(12):1891-1897 (1997).

U.S. Published Patent Application No. 2002/0076426 discloses terpene alcohol ethoxylates as solubilizers in pharmaceutical and food preparations.

Chinese Patent No. 1723981 discloses that an extract containing triterpene glycosides (mogrosides) isolated from *Momordica grosvenoiri* fruit was used to replace sucrose or other sweeteners in manufacturing pills, granules, tablets, capsules or solutions of traditional Chinese medicine.

DISCLOSURE OF INVENTION

I have discovered that mogroside V, paeoniflorin, and geniposide enhanced the solubility of a number of pharmaceutically and medicinally important compounds of several structural classes, including but not limited to, the important water-insoluble drugs of paclitaxel, camptothecin, curcumin, tanshinone IIA, amphotericin B, artemisinin, podophyllotoxin, silybin, propofol, celecoxib, clofazinine, digoxin, oleandrin, nifedipine, and amiodarone. The use of the above glycosides increased solubility of all tested compounds from about 2-fold to over 1000-fold, depending on the compound. In addition, certain diterpene glycosides (rubusoside, steviol monoside, stevioside, and rebaudioside A) were shown to enhance the solubility of clofazinine, digoxin, oleandrin, nifedipine, and amiodarone. The use of terpene glycosides as naturally occurring water solubility-enhancing compounds for specific drugs and compounds will be useful in the pharmaceutical, agricultural, cosmetic, and food industries.

BRIEF DESCRIPTION OF DRAWINGS

FIGS. 3A-3D illustrate the structure of representative diterpene glycosides, including rubusoside (FIG. 3A), stevioside (FIG. 3D), rebaudioside A (FIG. 3C), and steviol monoside (FIG. 3D).

Figure 14:
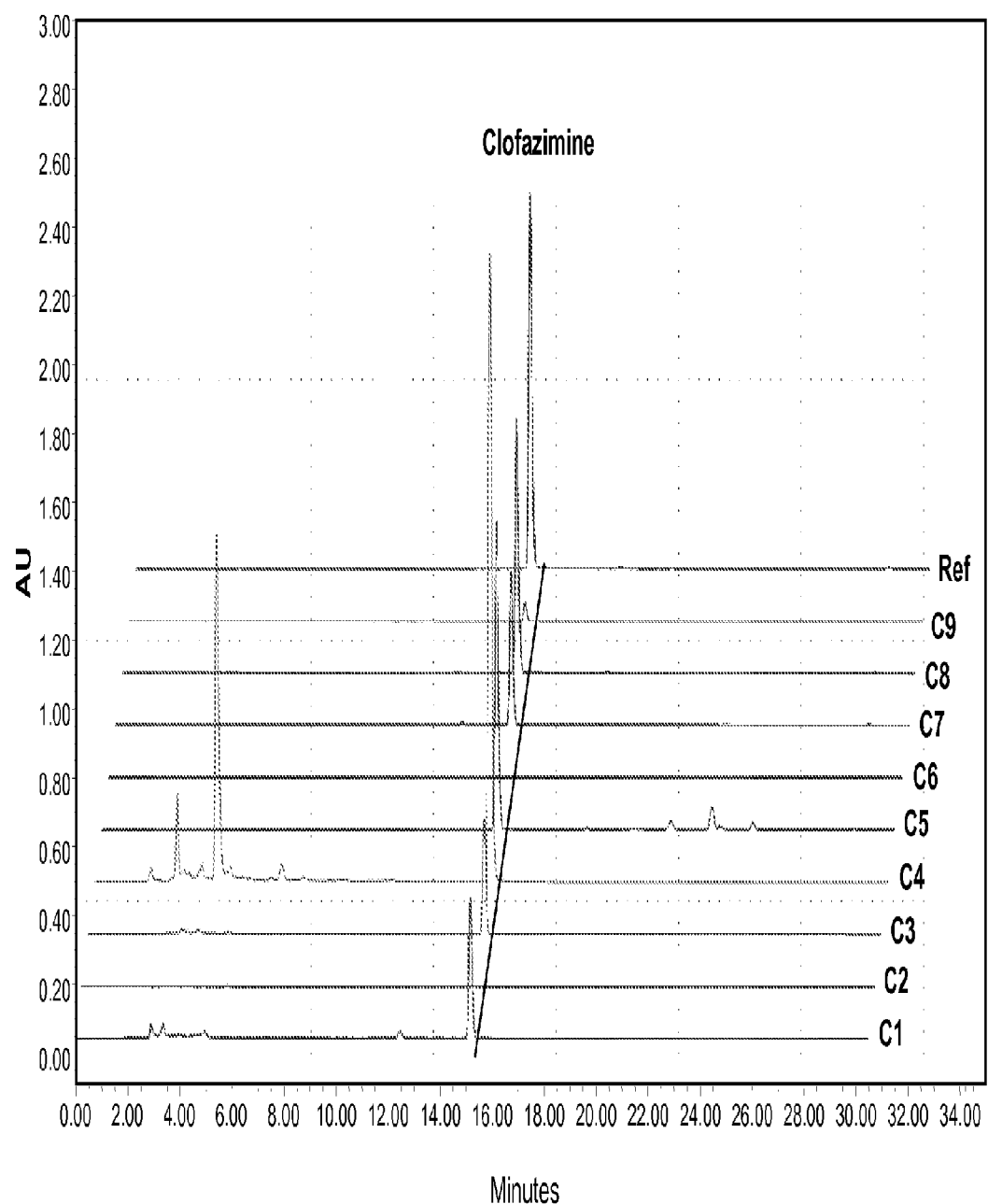

FIG. 14 illustrates the results of high performance liquid chromatography indicating the amount of dissolved clofazimine in ten solutions: C1, 10% mogroside V; C2, 10% astragaloside IV; C3, 10% geniposide; C4, 10% paeoniflorin; C5, 10% rubusoside; C6, 10% steviol monoside; C7, 10%, stevioside; C8, 10% rebaudioside A; C9, water (control); and Ref, 160 µg/ml clofazimine in methanol (reference standard).

Figure 15:
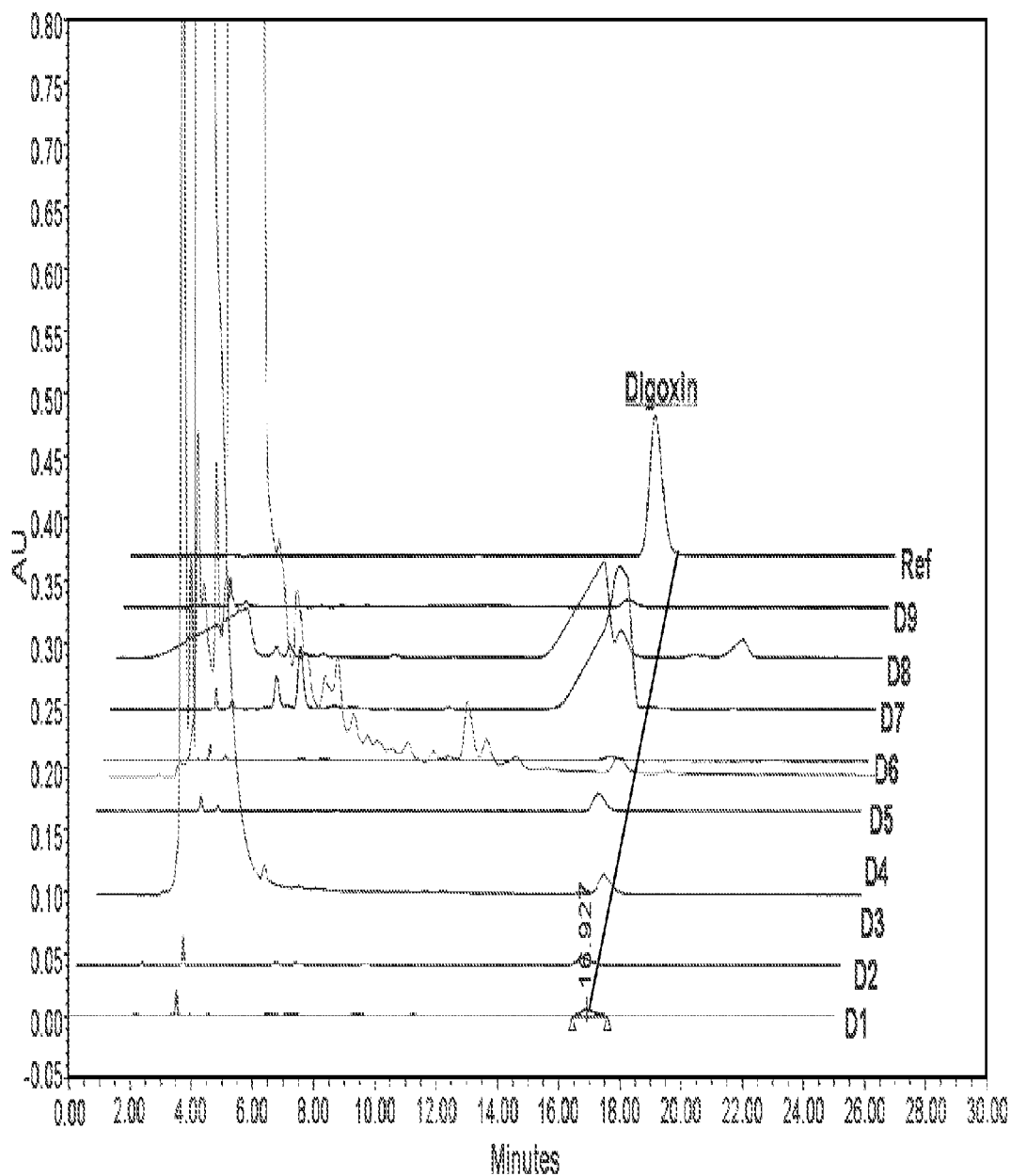

FIG. 15 illustrates the results of high performance liquid chromatography indicating the amount of dissolved digoxin in ten solutions: D1, 10% mogroside V; D2, 10% astragaloside IV; D3, 10% geniposide; D4, 10% paeoniflorin; D5, 10% rubusoside; D6, 10% steviol monoside; D7, 10%, stevioside; D8, 10% rebaudioside A; D9, water (control); and Ref, 388 µg/ml digoxin in methanol (reference standard).

Figure 16:
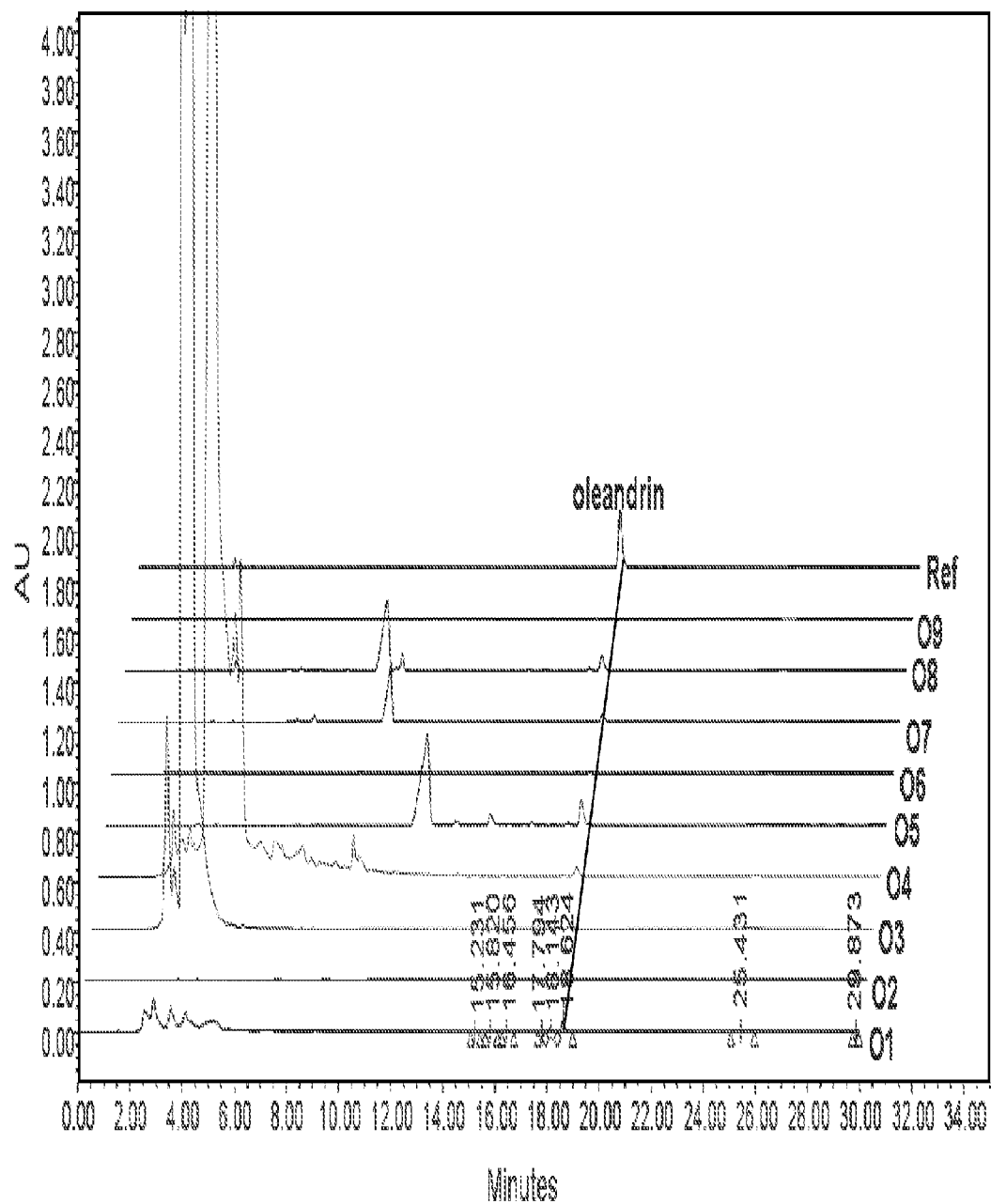

FIG. 16 illustrates the results of high performance liquid chromatography indicating the amount of dissolved oleandrin in ten solutions: O1, 10% mogroside V; O2, 10% astragaloside IV; O3, 10% geniposide; O4, 10% paeoniflorin; O5, 10% rubusoside; O6, 10% steviol monoside; O7, 10%, stevioside; O8, 10% rebaudioside A; O9, water (control); and Ref, 260 µg/ml oleandrin in methanol (reference standard).

Figure 17:
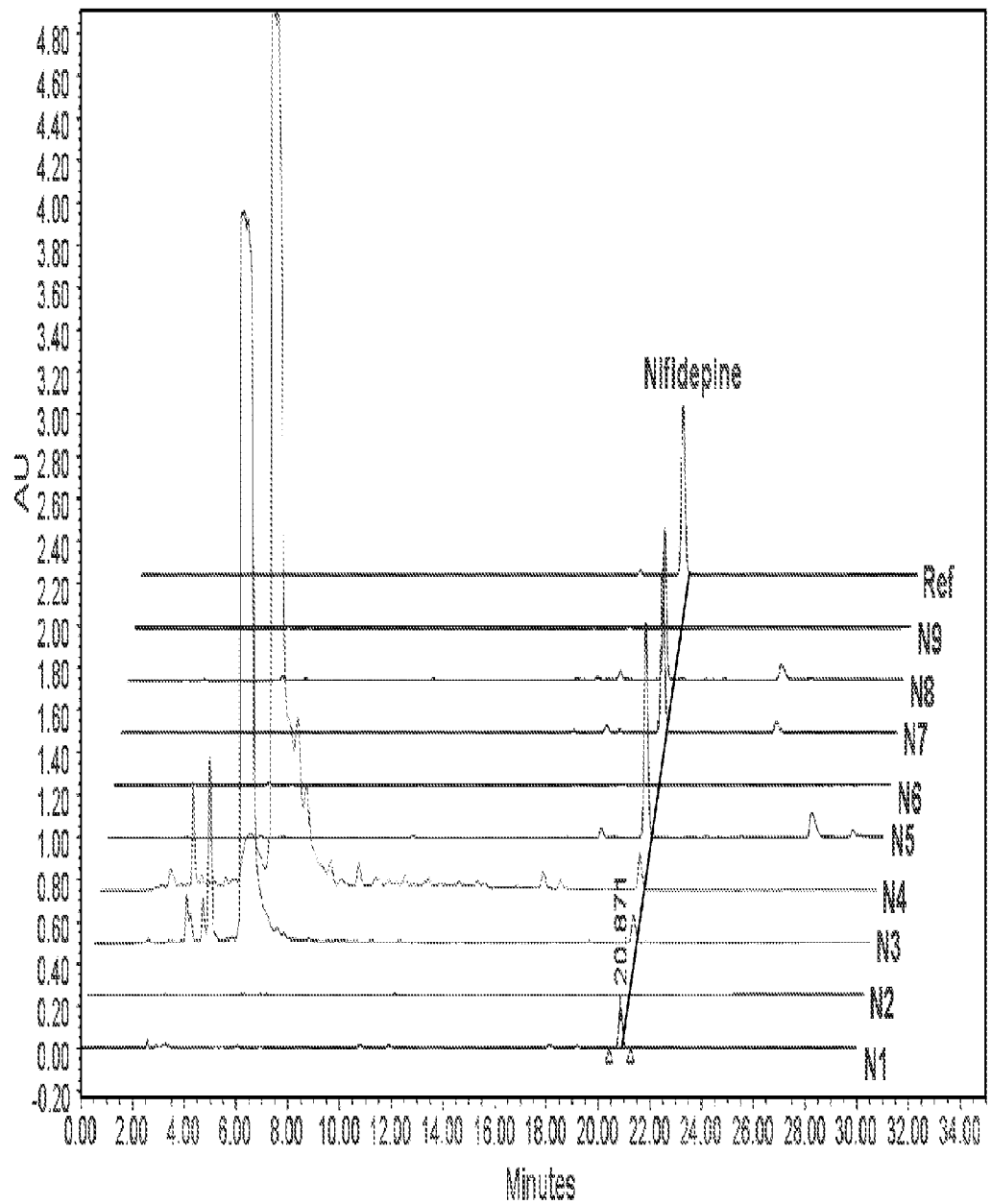

FIG. 17 illustrates the results of high performance liquid chromatography indicating the amount of dissolved nifidepine in ten solutions: N1, 10% mogroside V; N2, 10% astragaloside IV; N3, 10% geniposide; N4, 10% paeoniflorin; N5, 10% rubusoside; N6, 10% steviol monoside; N7, 10%, stevioside; N8, 10% rebaudioside A; N9, water (control); and Ref, 240 µg/ml nifidepine in methanol (reference standard).

Figure 18:
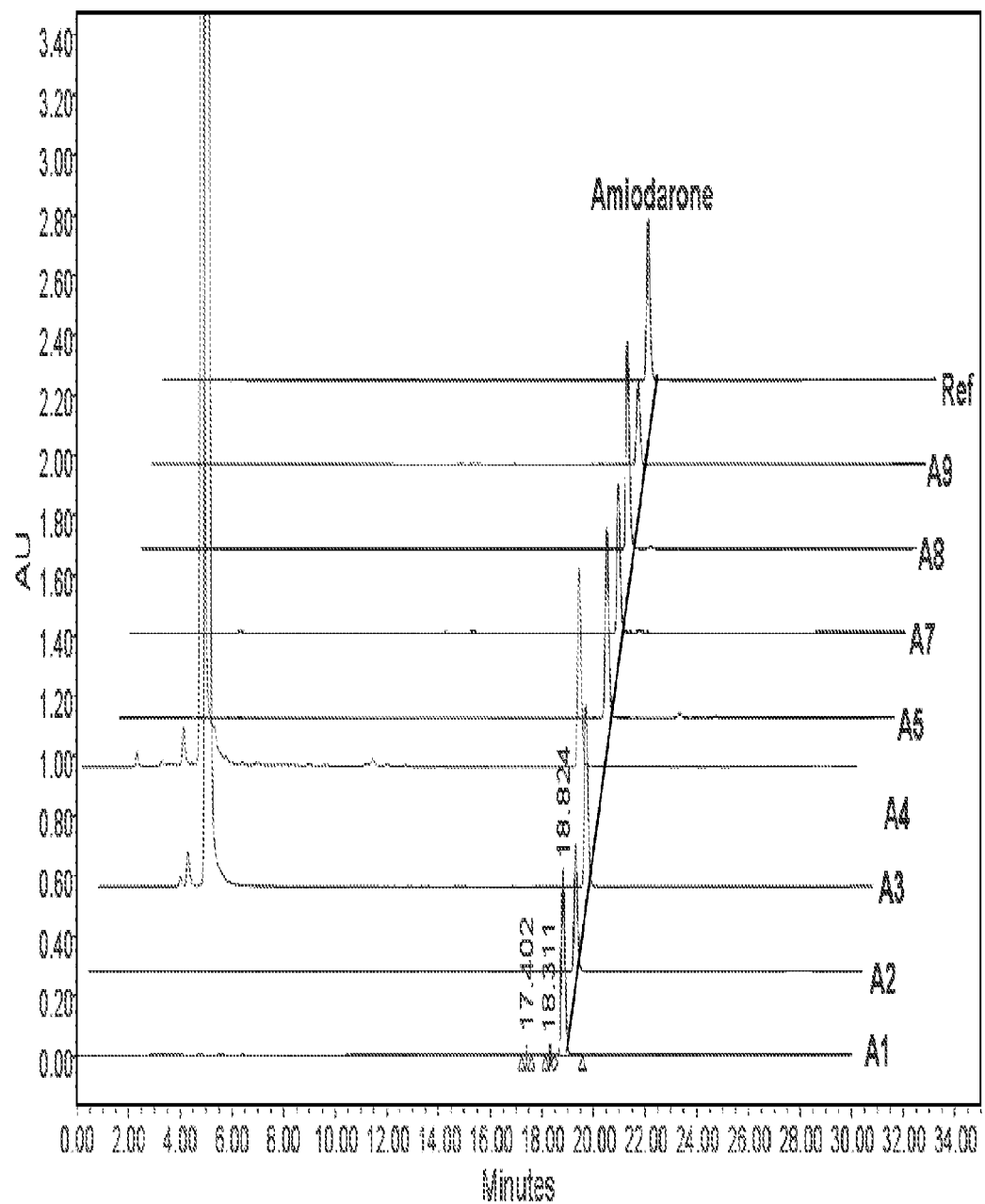

FIG. 18 illustrates the results of high performance liquid chromatography indicating the amount of dissolved amiodarone in ten solutions: A1, 10% mogroside V; A2, 10% astragaloside IV; A3, 10% geniposide; A4, 10% paeoniflorin; A5, 10% rubusoside; A6, 10% steviol monoside; A7, 10%, stevioside; A8, 10% rebaudioside A; A9, water (control); and Ref, 104 µg/ml amiodarone in methanol (reference standard).

MODES FOR CARRYING OUT THE INVENTION

Several important organic compounds are insoluble in water or have very low solubility. I have tested many of these therapeutic compounds from several classes of chemical structures and found that natural solubilizers based on terpene glycosides have increased the aqueous solubility of many compounds tested. I have found a method for enhancing the solubility of an organic compound which is insoluble or sparingly soluble in water, said method comprising mixing said compound with water and with a terpene glycoside in a concentration sufficient to increase the solubility of the compound in water by a factor of 2 or more. The solubility for the organic compounds in some cases has been increased by a factor of 5 or more, in others by a factor of 10 or more, in others by a factor of 20 or more, in others by a factor of 50 or more, in others by a factor of 100 or more, and in others by a factor of 1000 or more.

In addition, a new composition has been discovered comprising an aqueous solution of an organic compound having low solubility in water, and a terpene glycoside, selected from the group of mogroside V, paeoniflorin, geniposide, rubusoside, stevioside, and rebaudioside A; wherein the concentration of said terpene glycoside is sufficient to increase the solubility of said compound in water by a factor of 2 or more above what the solubility of said compound would be in an otherwise identical composition lacking said terpene glycoside. The solubility for the organic compounds in some cases has been increased by a factor of 5 or more, in others by a factor of 10 or more, in others by a factor of 20 or more, in others by a factor of 50 or more, in others by a factor of 100 or more, and in others by a factor of 1000 or more. The solubilizers can be used in concentrations from 1% to 100% w/v, depending on the solubility of each solubilizer in water. The solubilzer solutions were found to be particularly effective from about 5 to about 40% w/v solubilizer, preferable about 10% w/v solubilizer. The concentration of the solubilizer will determine the amount of the drug that will be dissolved. Thus the concentration will depend on the desired dose of the drug to be administered.

I have discovered several terpene glycosides as new solubilizing agents for creating new pharmaceutical, cosmetic, agricultural and food formulations instead of the commonly used cyclodextrins. Without being bound by this theory, it is believed that the improved solubility of water-insoluble drugs is a result of the formation of terpene glycoside (TGs)-drug complex structures, such as nano- to micro-size micelles, which are water soluble. The driving forces for the formation of the dTG-drug complexes may include London dispersion forces (an induced dipole-induced dipole attraction), dipolar forces (including hydrogen-bonding), ionic (electrostatic) forces, and/or hydrophobic effects as described in R. Liu, Water-insoluble drug formulation, Second Edition, pp 133-160, 2008, CRC Press, Boca Raton, Fla. Depending on the drug molecule, solubilization power of the TGs will vary depending on the driving force in forming each intermolecular complexation.

Without being bound by this theory, it is believed that the formation of the TG-drug complexes in aqueous solutions may be driven by similar forces proposed for cyclodextrins (CDs) in the formation of inclusion complexes, by the surfactant property, or by both. In addition to the driving forces above, van der Waals forces (the attractive or repulsive force between molecules or between parts of the same molecule) may be involved. The difference between the CD-drug inclusion complexes and the TG-drug complexes may be attributable to their geometrical structures. Rather than forming a circle with a hydrophobic cavity similar to the CDs, the TGs may form uniform and dynamic structures, with the hydrophilic glucose molecules exposing to water and with the hydrophobic terpene aglycones in the center as the spacer sites that host water-insoluble drug molecules.

The new complexing or micellating agents, terpene glycosides (TGs), have several advantages over CDs as complexing agents. First, TGs may be less rigid on the requirement of the cavity size, which has been a limiting factor for the formation of β-CDs-drug complexes, especially large molecular drugs. Second, the possible uniformity of hydrophilic-hydrophobic spacing alignment of TGs may be more efficient than the circular hydrophilic-hydrophobic spacing alignment, and thus capable of solubilizing more drug molecules. Third, the TGs have excellent water solubility and stability in water solution. The solubility of some TGs can be as high as about 60 g/100 mL in water at 25° C. and about 80 g/100 mL in water at 37° C. This is much higher than β-CD of 1.85 g/100 mL water, α-CD of 15 g/100 mL water, or γ-CD of 23 g/100 mL water. In addition, many of the terpene glycosides may actually be safer for internal injections. Some diterpene glycosides have been approved by the FDA as sweeteners (e.g., rebaudioside A). Based on the aglycone steviol, estimates are that daily consumption of steviol glycosides of 8 mg rubusoside/kg body weight is safe and has no adverse effect, and up to 766 mg rubusoside/kg body weight (based on 383 mg/kg body weight daily expressed as steviol) is the no-observed-effect level. The intraperitoneal injection of stevioside water solution in hypertensive rats at doses of 50 mg/kg and 100 mg/kg body weight showed no adverse effects (Y.-H. Hsu et al., Antihypertensive Effect of Stevioside in Different Strains of Hypertensive Rats. Chinese Medical Journal (Taipei) 2002; vol. 65:1-6). In pharmaceutical dosing paradigm, 50 mg/kg or less of rubusoside or other terpene glycosides may be sufficient to solubilize drugs to therapeutic levels for parental applications. Additionally, the geometry of terpene glycosides as complexing or micellating agents to increase solubility of water-insoluble drugs may increase bioavailability by readily exposing the drug molecules to the bi-layer membranes of the target cells for rapid absorption. Moreover, the formed rubusoside-curcumin complexes in water solutions were shown resistant to heat up to 121° C. and pH changes from acid to alkaline conditions. Last, the heat stability of certain terpene glycosides up to 250° C. allows effective use of melting and other heating methods in the preparation of solid complexes. Based on the above comparisons, features, and experimental data shown in this invention, it is believed that the TGs are superior to CDs as complexing agents in the solubilization of water-insoluble drugs. In addition, various combinations of TGs could be used as solubilizers to further increase the solubility of a given drug.

Using the terpene glycosides as solubilizers provides a way to alleviate problems with low solubility drugs, e.g., low absorption and low bio-availability of the drug. In addition, using the solubilizer and drug in a powder form (containing solubilizer-drug complexes) will allow solid formulations that are readily dissolvable in water, e.g., tablet or even effervescent tablets. The solubilizers can be used to prepare non-alcoholic syrups of low solubility drugs that are stable, or to prepare gelatin capsules with the solubilizer and drug inside.

The solubilizer (terpene glycoside) and solubilized drug may be administered to a patient by any suitable means, including oral, parenteral, subcutaneous, intrapulmonary, topical (e.g., ocular or dermal), rectal and intranasal administration. Parenteral infusions include intramuscular, intravenous, intraarterial, or intraperitoneal administration. The solution or its dry ingredients (containing solubilizer-drug complexes) may also be administered transdermally, for example in the form of a slow-release subcutaneous implant, or orally in the form of capsules, powders, or granules.

Pharmaceutically acceptable carrier preparations for parenteral administration include sterile, aqueous or non-aqueous solutions, suspensions, and emulsions. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. The solubilizer and drug may be mixed with other excipients that are pharmaceutically acceptable and are compatible with the active ingredient in the drug. Suitable excipients include water, saline, dextrose, glycerol and ethanol, or combinations thereof. Intravenous vehicles include fluid and nutrient replenishers, electrolyte replenishers, such as those based on Ringer's dextrose, and the like. Preservatives and other additives may also be present such as, for example, antimicrobials, anti-oxidants, chelating agents, inert gases, and the like.

The form may vary depending upon the route of administration. For example, compositions for injection may be provided in the form of an ampule, each containing a unit dose amount, or in the form of a container containing multiple doses, or in the form of powder that is reconstituted with a suitable solvent (e.g., saline solution) prior to injection.

For purposes of this application, a compound that is insoluble in water is a compound in which less than 100 μg dissolves in 1 mL water. A compound that is sparingly soluble in water is one in which less than 20 mg, but more than 100 μg, dissolves in 1 mL water. Finally, in general, a compound that has low solubility in water is one in which less than 20 mg dissolves in 1 mL water.

Figure 1I:
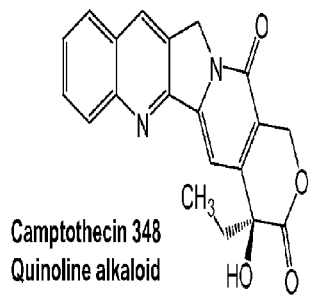
FIGS. 1A to 1P illustrates the structures of representative compounds of several classes of compounds that are known to have low water solubility, and that have been shown to be solubilized using a terpene glycoside, including curcumin (FIG. 1A), tanshinone IIA (FIG. 1B), Coenzyme-Q10 (FIG. 1C), artemisinin (FIG. 1D), podophyllotoxin (FIG. 1E), silybin (FIG. 1F), digoxin (FIG. 1G), oleandrin (FIG. 1H), camptothecin (FIG. 1I), paclitaxel (FIG. 1J), amphotencin (FIG. 1K), propofol (FIG. 1L), celecoxib (FIG. 1M), clofazimine (FIG. 1N), nifedipine (FIG. 1O), and amiodarone (FIG. 1P).
Figure 1J:
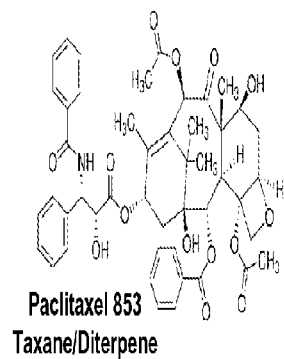
Figure 1K:
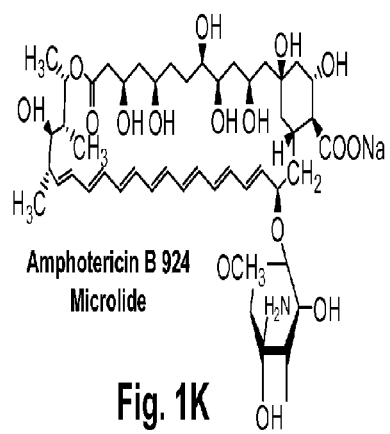
Figure 1L:
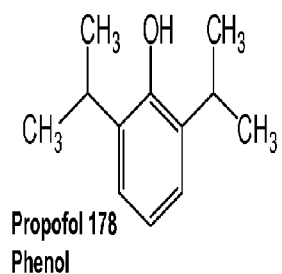
Figure 1M:
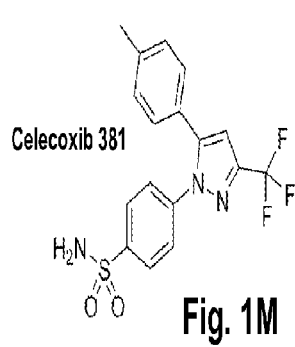
Figure 1N:
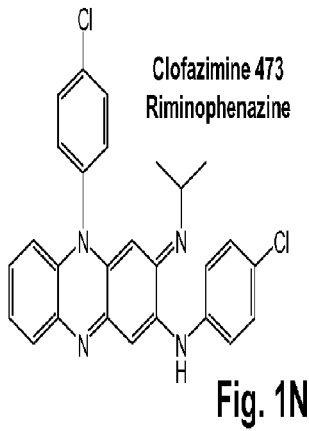
Figure 1O:
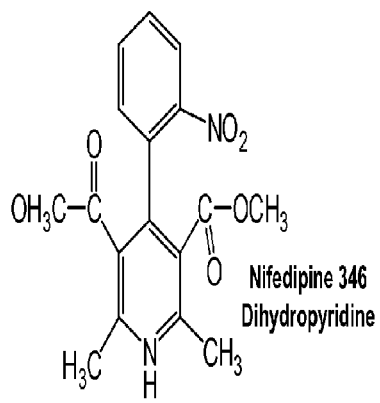
Figure 1P:
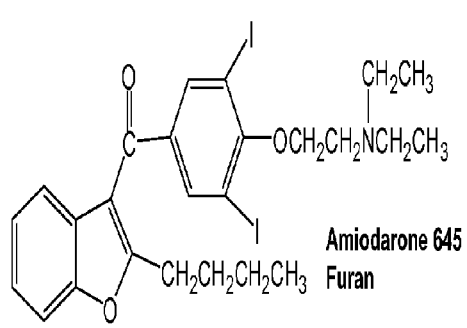

The structures of representative compounds of the various classes of organic compounds with low solubility are shown in FIGS. 1A to 1P. A summary of some of the experimental data using these compounds and several natural terpene glycosides is given in Table 1. The details of these experiments, including results from control experiments, are given below.

TABLE 1

Active Pharmaceutical Ingredients (APIs) in Water Solutions Containing 10% w/v Natural Solubilizing Compounds

| Organic Compound | M.W. | Solubility in water without solubilizer (μg/mL) | With Mogroside V μg/mL | With Astragaloside μg/mL | With Geniposide μg/mL | With Paeoniflorin μg/mL | With Rubusoside μg/mL | With Steviol monoside μg/mL | With Stevioside μg/mL | With Rebaudioside A μg/mL |
|---|---|---|---|---|---|---|---|---|---|---|
| Curcumin | 348 | 0.6[1] | 44 | 0 | 4 | 5 | 262 | 4 | NE[3] | NE[3] |
| Tanshinone IIA | 294 | 0[2] | 0.5 | 0 | 0.1 | 23 | 127 | NE[3] | NE[3] | NE[3] |
| Coenzyme Q10 | 863 | 0.1[1] | 0 | 0 | 0 | 0 | 111 | NE[3] | NE[3] | NE[3] |
| Camptothecin | 348 | 0.4[1] | 18 | NE[3] | 25 | 53 | 61 | NE[3] | NE[3] | 48 |
| Paclitaxel | 853 | 0.35[1] | 7 | NE[3] | 1 | 20 | 65 | NE[3] | NE[3] | 26 |
| Amphotericin B | 924 | 0[2] | 6 | 0 | 0.2 | 19 | 200 | NE[3] | NE[3] | NE[3] |
| Artemisinin | 282 | 53[2] | 148 | 0 | 146 | 218 | 280 | NE[3] | NE[3] | NE[3] |
| Podophyllotoxin | 414 | 9[2] | 747 | 0 | 644 | 586 | 919 | NE[3] | NE[3] | NE[3] |
| Silybin | 482 | 0[2] | 18 | 0 | 16 | 37 | 150 | NE[3] | NE[3] | NE[3] |
| Propofol | 178 | 0[2] | 56 | 0 | 7 | 349 | 11700 | NE[3] | NE[3] | NE[3] |
| Celecoxib | 381 | 0[2] | 47 | 0 | 3 | 253 | 488 | NE[3] | NE[3] | NE[3] |
| Clofazimine | 473 | 7.6[2] | 58 | 0.4 | 48 | 565 | 132 | 0 | 64 | 109 |
| Digoxin | 780 | 19[2] | 35 | 18 | 26 | 38 | 48 | 10 | 30 | 32 |
| Oleandrin | 576 | 3[2] | 47 | 5 | 28 | 42 | 123 | 7 | 74 | 67 |
| Nifedipine | 346 | 0[2] | 55 | 0 | 39 | 49 | 286 | 0 | 468 | 203 |
| Amiodarone | 645 | 107[2] | 238 | 164 | 235 | 250 | 249 | 0 | 201 | 271 |

[1]Solubility values are obtained from MSDS, Merck Index, or publications;
[2]Solubility values were determined by my own analysis;
[3]NE—Not examined.

Example 1

Materials and Methods

Sources of Solubilizers

Figures 3A, 3B:
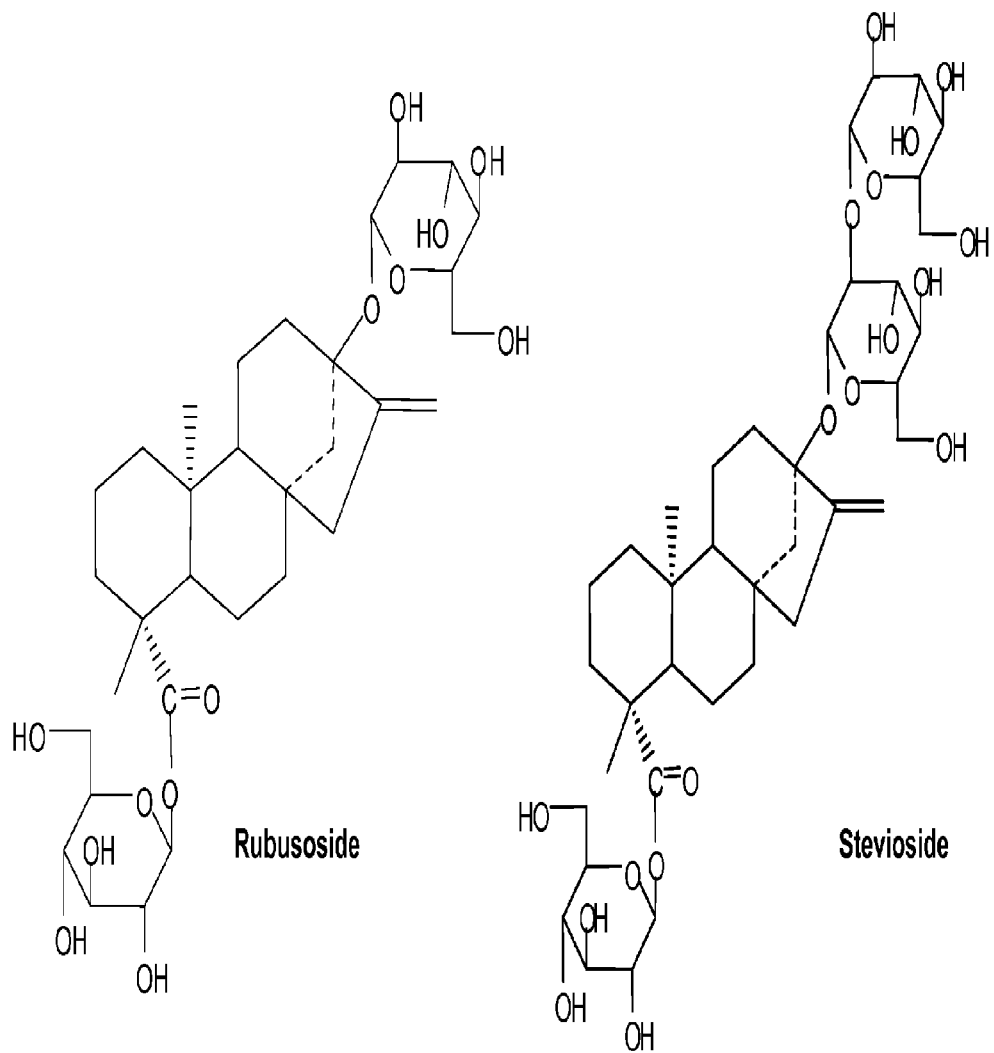

Rubusoside:

Rubusoside was extracted from Chinese sweet leaf tea leaves (*Rubus suavissimus*; Rosaceae) purchased from Natural Plants Products Factory, Guilin S&T New Tech Company, Sanlidian Campus of Guangxi Normal University, Guilin, Guangxi, China. Rubusoside has a molecular formula $C_{32}H_{50}O_{13}$ and molecular weight of 642.73. First, the air-dried leaves were boiled with water with a weight to volume ratio ranging from about 1:10 to about 1:20. From this extraction, a crude dried extract (20 to 30% dry weight yield from the raw leaves) was obtained that contained from about 5% to about 15% rubusoside by weight. The dried extract was then reconstituted with water to a weight to volume ratio ranging from about 1:4 to about 1:5. In this concentrated extract, the ellagitannins would partially precipitate out and were removed by filtration. The rubusoside was retained in the solution. The solution containing rubusoside was then subjected to column chromatography using a macroporous resin (Dowex Optipore L493 Polymeric Adsorbent, Styrene-Divinylbenzene polymers with 46 Angstrom average pore size; The Dow Chemical Company, Midland, Mich.). The column was eluted with ethanol to obtain a purified extract containing approximately 60% rubusoside and about 1% steviol monoside. Some of this extract was used in Example 16 below. Subsequently, the purified extract was loaded on a second column to further purify the extract using silica gel as the stationary absorbent (Silica Gel, 200-300 mesh, Natland International Corporation, Research Triangle, N.C.). The column was eluted with a mixed solvent (chloroform:methanol at a ratio of 8:2 v/v). The extract from this second column was at least 80% pure rubusoside, and was dried to a powder. Finally, this rubusoside-rich extract (>80% w/w) was dissolved in absolute methanol by heating to temperatures ranging from about 60° C. to about 80° C. The solution was then cooled to allow re-crystallization of rubusoside. This re-crystallization process may need to be repeated to obtain pure rubusoside (>99% purity as measured on HPLC). The structure of rubusoside was confirmed by mass spectrometry and NMR. Rubusoside, a diterpene glycoside, has a molecular weight of 642 Daltons, and is a white crystal or powder. The structure is shown in FIG. 3A. The crystalline powder is stable at temperatures ranging from about −80° C. to over 100° C. In water, rubusoside itself has a solubility of approximately 400 mg/ml at 25° C. and 800 mg/ml at 37° C., which is greater than that of many common, water-soluble compounds (e.g., sodium chloride has a solubility of 360 mg/ml water).

Stevioside:

Stevioside is a diterpene glycoside that is isolated from the *Stevia* leaf (*Stevia rebaudiana*; Asteraceae). Stevioside has a molecular formula $C_{38}H_{60}O_{18}$ and a molecular weight of 804. The structure is shown in FIG. 3B. Stevioside was purchased from Chromadex Inc. (Irvine, Calif.).

Rebaudioside A:

Rebaudioside A is a diterpene glycoside that is isolated from the *Stevia* leaf (*Stevia rebaudiana*; Asteraceae). Its structure is shown in FIG. 3C. Rebaudioside A was purchased from Chromadex Inc. (Irvine, Calif.).

Steviol Monoside:

Steviol monoside is a diterpene glycoside that is isolated from the Chinese sweet leaf tea (*Rubus suavissimus*; Rosaceae), the same source as rubusoside. The structure of steviol monoside has only one glucose moiety (FIG. 3D) rather than two as in rubusoside (FIG. 3A). Steviol monoside can be isolated from the sweet leaf tea or be obtained through the acid hydrolysis of rubusoside to cleave one glucose unit.

Figures 2A, 2B:
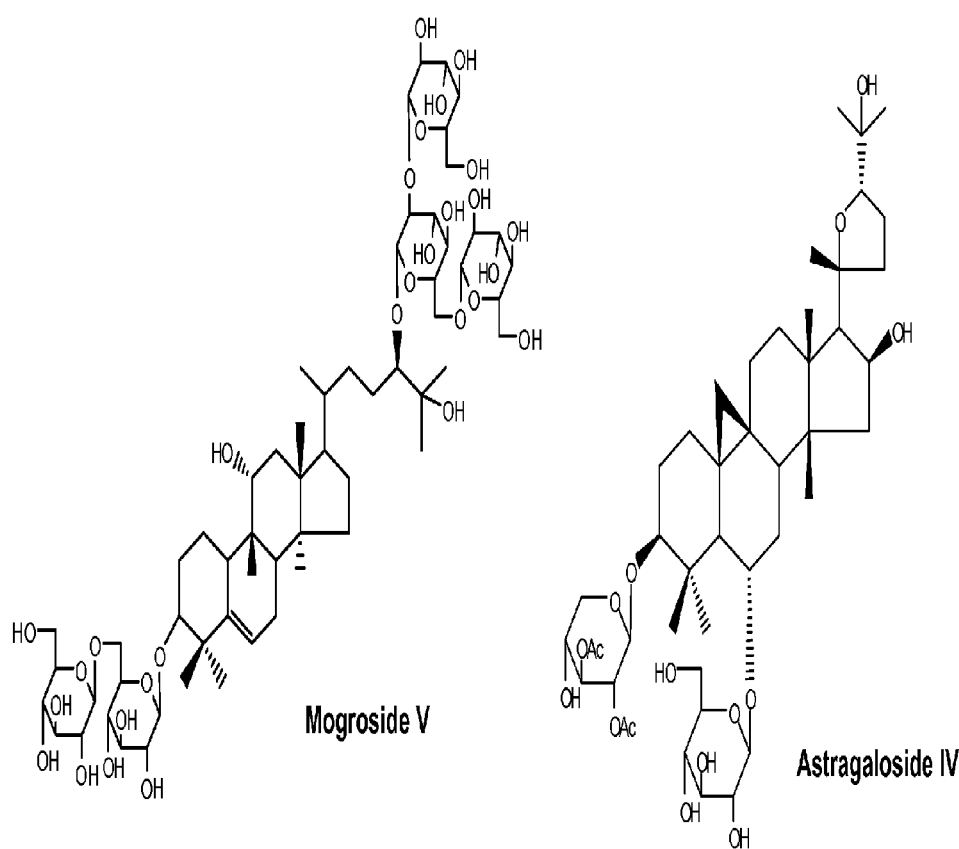
FIGS. 2A-2D illustrate the structure of some representative triterpene glycosides (mogroside V, FIG. 2A; and astragaloside, FIG. 2B) and monoterpene glycosides (paconiflorin, FIG. 2C; and geniposide, FIG. 2D).
Figure 2C:
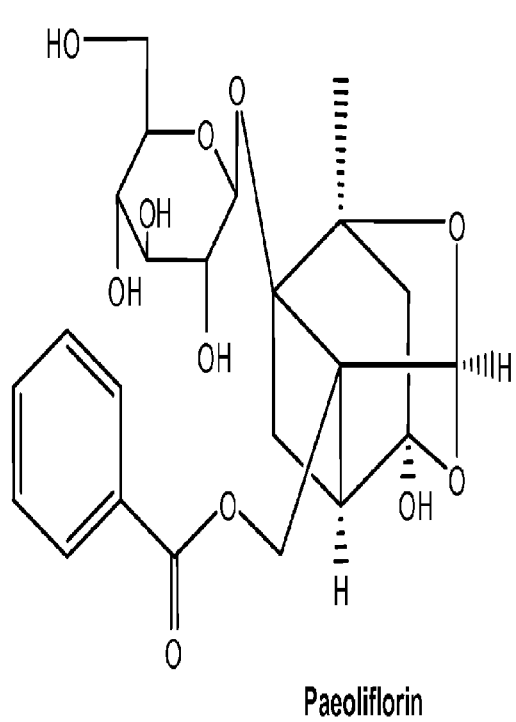
Figure 2D:
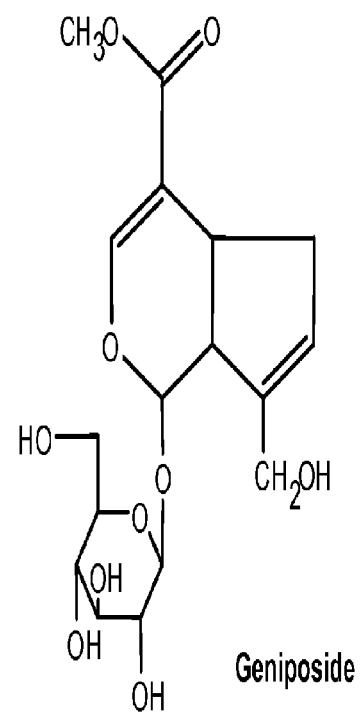

Geniposide:

Geniposide is a monoterpene glycoside and was purchased from Shanghai University of Traditional Chinese Medicine (Shanghai, China). Its structure is shown in FIG. 2D.

Paeoniflorin:

Paeoniflorin is a monoterpene glycoside and was purchased from Shanghai University of Traditional Chinese Medicine (Shanghai, China). Its structure is shown in FIG. 1C.

Mogroside V.

Mogroside V is a triterpene glycoside that is isolated from the luohanguo fruit (*Momordica grosvenori*; Curcubitaceae). The structure of mogroside V is shown in FIG. 2A. A mogroside V-rich extract (>25% by weight) was purchased from Guangxi Normal University, Guilin, China, and was used in the solubility experiments. Initial purification resulted in a powder containing 80% mogrosides. With further isolation and purification, a purified mogroside V (>95% purity based HPLC-UV) was obtained. This purified mogroside V was used in the solubility experiments. The purification procedure is described below. First, 45 g of the extract was extracted with 900 ml methanol with ultrasonication for 30 min twice. Then it was filtered with Whatman #4 paper filter. The filtrate was concentrated and mixed with 25 g silica gel. The solvent was removed to obtain the dried mixed sample. The dried mixed sample was loaded onto the top of a prepared chromatography column with 600 g silica gel and a mobile phase of chloroform-methanol-water (8:2:0.2). Then it was subjected to chromatography with gradient mobile phase (from water to chloroform-methanol-water at 5:5:0.5 ratio). The fractions every 500 ml were collected. Fractions that indicated similar chromatograms using TLC monitoring were combined. Mogroside V was found in high concentration in Fraction 53~66 with light yellow color. (Data not shown) These fractions were combined, and 5 g active carbon was added. The mixture was ultrasonicated for 30 min, and then filtered with Whatman #4 paper filter twice. The filtrate was concentrated, and subjected to Sephadex chromatography with methanol. Sub-fractions were collected based on peaks monitored at 205 nm. The collected fractions with similar peaks were combined and concentrated. The concentrate was dissolved in 20 ml water, and the aqueous solution collected to a centrifuge tube and freeze-dried to obtain a white powder (7.59 g). The final powder was analyzed with HPLC to confirm its purity as >95% mogroside V. MS data shows its molecular ion ($MH^+$) is 1287.6616 (calculated 1287.6579, 2.83 ppm in error) and molecular formula is $C_{60}H_{103}O_{29}$. NMR data was collected and compared to a published reference (Data not shown). See Y. Xiuwei and Z. Jianye, NMR structural elucidation of mogrol and its glycosides, Chinese Journal of Magnetic Resonance, 2007, 24(3): 250-260.

Astragaloside IV:

Astragaloside is a triterpene glycoside and was purchased from Shanghai University of Traditional Chinese Medicine (Shanghai, China). Its structure is shown in FIG. 1B. It is not very soluble in water (estimated to be about 30 mg/ml in water or 3% w/v), and was shown below not to be an effective solubilizer for drugs.

Compounds Tested for Solubility:

Sixteen bioactive and pharmaceutical compounds with a water solubility ranging from poorly soluble (200 μg/mL) to insoluble (0.01 μg/ml) were used. All compounds were found to have purity greater than 98% based on HPLC (unless otherwise indicated). Their chemical structures are shown in FIGS. 1A-1P. Tanshinone IIA was purchased from Shanghai University of Traditional Chinese Medicine (Shanghai, China) and is nearly insoluble. Curcumin, camptothecin, and paclitaxel were all purchased from Sigma-Aldrich Chemicals (St. Louis, Mo.). Artemisinin, podophyllotoxin, and silybin (Silibinin) were purchased from LKT Laboratories (St. Paul, Minn.). According to The Merck Index (1996), the solubilities of these compounds are as follows: curcumin (insoluble), camptothecin (insoluble), and paclitaxel (insoluble). According to the Material Safety Data Sheets, artemisinin, podophyllotoxin, and silybin (Silibinin) have a water solubility of insoluble, nearly insoluble, poor, and insoluble, respectively.

An antifungal compound (Amphotericin B) was tested. It was purchased from Sigma-Aldrich Chemicals (St. Louis, Mo.) and is nearly insoluble. Moreover, two lipid soluble compounds were tested: Coenzyme Q10 was purchased from MP Biomedicals Inc. (Solon, Ohio), and propofol were purchased from Sigma-Aldrich Chemicals (St. Louis, Mo.). The water insoluble celecoxib was purchased from LC Laboratories (Woburn, Mass.).

Digoxin and clofazimine were purchased from Sigma-Aldrich Chemicals (St. Louis, Mo.) and are practically insoluble in water (The Merck Index, $14^{th}$ Edition, 2006). Oleandrin was purchased from Shanghai University of Traditional Chinese Medicine (Shanghai, China) and is practically insoluble in water (The Merck Index, $14^{th}$ Edition, 2006). Nifedipine and amiodarone were purchased from LKT Laboratories (St. Paul, Minn.) and are nearly insoluble in water.

Solubility Test Methods:

A compound with low solubility was selected and weighed into multiple centrifuge tubes. Each experimental tube received a known amount of the solubilizing agent being tested. The control tubes remained only with the compound. The same volume, 1 mL, unless otherwise indicated, of deionized, distilled water was added to each tube. Alternatively, a set percentage of water solutions containing the solubilizer to be tested (e.g., 10% w/v) were prepared separately. In these cases, the solubilizer-water solutions were added directly to the tubes containing the low-solubility compound. The tubes were then vortexed briefly and then sonicated for 60 min at temperature of 50° C. After sonication, the tubes were placed in an incubator set at 25° C. for at least 72 hr. The tubes were then centrifuged at 4000 rpm for 10 min. The supernatant solution was passed through a 0.2 μm filter and analyzed for the concentration of the low-solubility compound by HPLC or LC/MS.

HPLC-UV and HPLC-MS Analysis:

The solutions containing various compounds in the absence or presence of solubilizers were analyzed on HPLC-UV or HPLC-MS which consisted of a solvent delivery pump unit, an autosampler (Waters 717 plus), a UV-Vis diode array detector (Waters 2996 Photodiode Array Detector, 190 to 800 nm) coupled with an EMD 1000 Mass Detector (Waters), and an evaporative light-scattering detector (Waters 2420 ELSD). The system was computer controlled, and the results were analyzed using Empower software. Calibrations curves were constructed using known concentrations of the compounds and were used to quantify the concentrations of the compounds dissolved in solution.

Example 2

Figure 4:
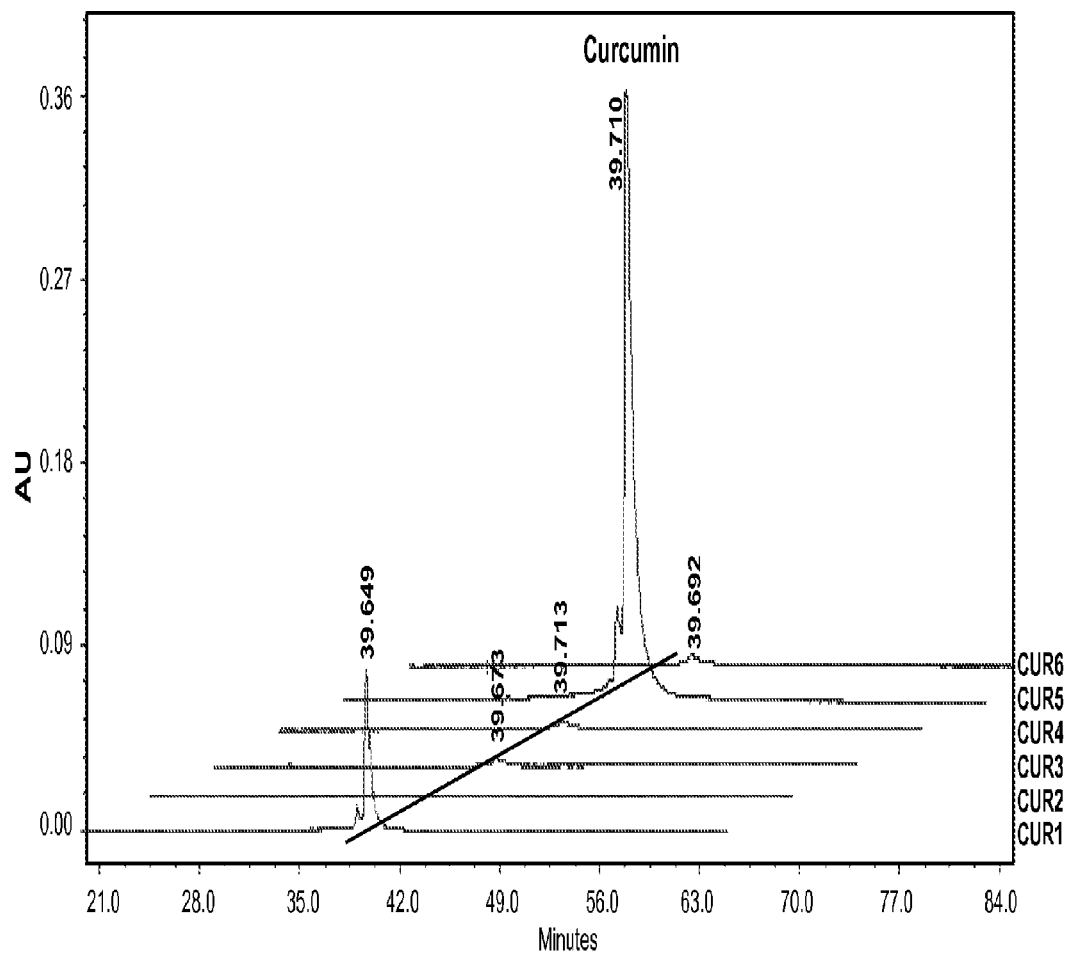
FIG. 4 illustrates the results of high performance liquid chromatography indicating the amount of dissolved curcumin in six solutions: CUR1, 10% mogroside V; CUR2, 10% astragaloside; CUR5, 10% geniposide; CUR4, 10% paconiflorin; CUR5, 10% rubusoside; and CUR6, 10% steviol monoside.

Effect of Mogroside V, Astragaloside IV, Geniposide, or Paeoniflorin on the Water Solubility of Curcumin A 10% w/v of mogroside V (1), astragaloside IV (2), geniposide (3), paeoniflorin (4), rubusoside (5), or steviol monoside (6) water solution was each prepared. Astragaloside IV at 10% w/v showed precipitation; therefore, the water solution contained less than 10% astragaloside IV. One set of two milligrams of curcumin was weighed into separate centrifuge tubes. The solutions were sonicated at 50° C. for 60 min followed by incubation at 25° C. for 72 hr. These compounds in the solubilized water solutions were filtered by 0.45 μM filters and analyzed on HPLC. Quantification was done by comparing to a standard solution of a known amount in methanol. The chromatograms of six curcumin water solutions (CUR1-CUR6) containing 10% w/v natural solubilizers (1-6: mogroside V, astragaloside, geniposide, paeoniflorin, rubusoside, and steviol monoside) as complexing agents, respectively, are shown in FIG. 4. The HPLC system included 600 pump, 717 autosampler, and 2996 PDA. The chromatograms were generated using a Prevail C18 column (4.6×250 mm, 5 μm) and a mobile phase of 0.02% HCOOH-ACN (A): 0.02% HCOOH—H20 (B), the gradient was A from 20% to 80% in 45 min; at a flow rate of 1.0 mL/min, injection volume of 5 μL, UV detection wavelength of 425 nm, and column temperature of 30° C. Curcumin concentration was determined using a standard curcumin calibration curve with curcumin standard solutions of 2.12, 21.2, and 212 μg/ml. The chromatograms of CUR1-CUR6 above were generated at 425 nm UV showing elution of curcumin at 39.7 min, the peak areas of which were used for quantification of curcumin. The contents of astragaloside and steviol monoside in solutions were less than 10% as judged by their precipitations in the water solutions. In the presence of 10% w/v of mogroside V (CUR1), astragaloside IV (CUR2), geniposide (CUR3), paeoniflorin (CUR4), rubusoside (CUR5), or steviol monoside (CUR6), the water solutions contained 44 μg/mL, 0 μg/mL, 4 μg/mL, 5 μg/mL, 262 μg/mL, and 4 μg/mL curcumin, respectively (FIG. 4). Rubusoside was the best solubilizer for curcumin.

Example 3

Effect of Mogroside V, Geniposide, Paeoniflorin or Rebaudioside A on the Water Solubility of Camptothecin and Paclitaxel Ten percent w/v of mogroside V (1), geniposide (3), paeoniflorin (4), rebaudioside A (8), or a water control containing no solubilizing agents (9) water solutions was each prepared. One set of two milligrams of camptothecin or paclitaxel were weighed into separate centrifuge tubes, and received one of the solubilizing agent 1, 3, 4, 8, or 9 (control). These water solutions were sonicated at 50° C. for 60 min followed by incubation at 25° C. for 72 hr. These compounds in the solubilized water solutions were filtered by 0.45 μM filters and analyzed on HPLC. Quantification was done by comparing to a standard solution of a known amount in methanol.

Figure 5:
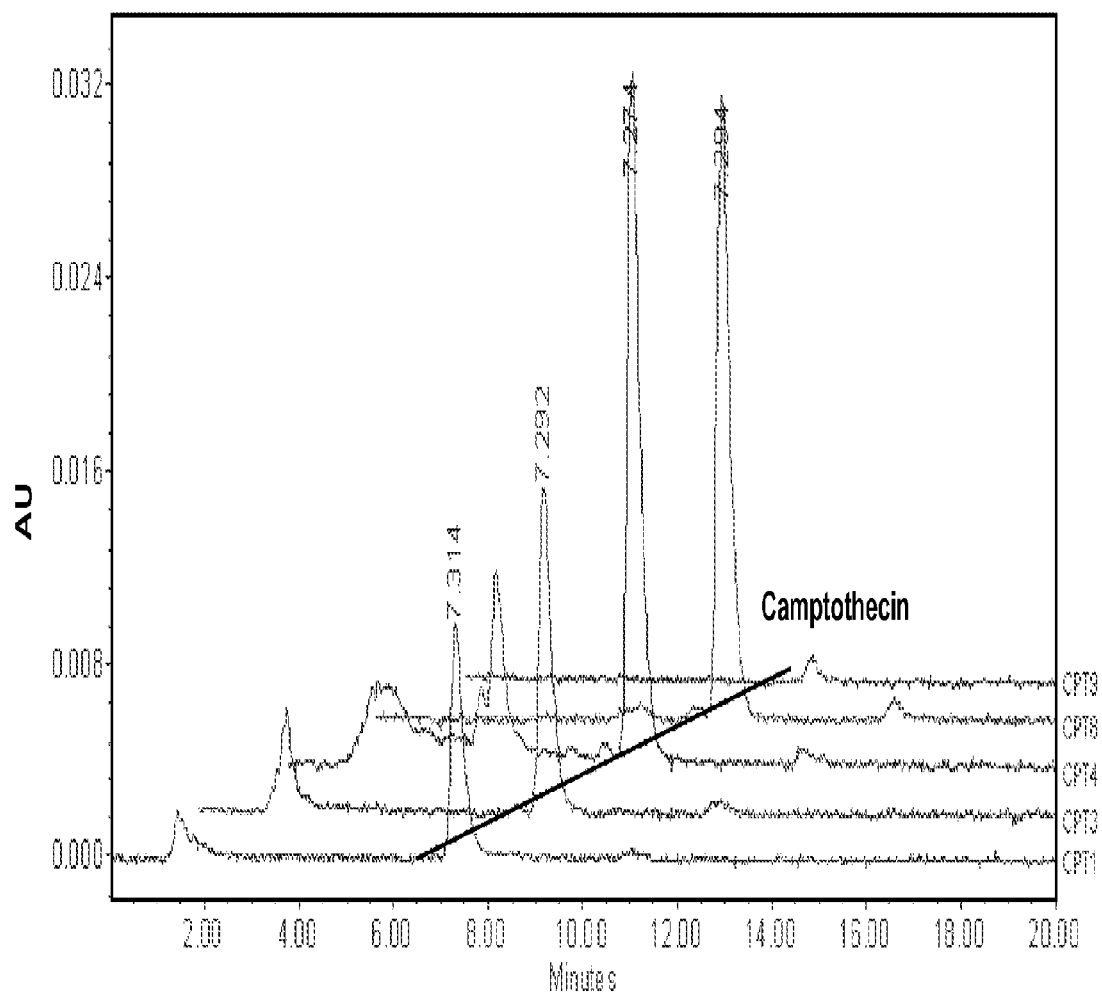
FIG. 5 illustrates the results of high performance liquid chromatography indicating the amount of dissolved camptothecin in five solutions: CPT1, 10% mogroside V; CPT3, 10% geniposide; CPT4, 10% paconiflorin; CPT8, 10% rebaudioside A; and CPT9, water (control).

Camptothecin:

Chromatograms of five camptothecin water solutions. CPT1, CPT3, CPT4, and CPT8 containing 10% w/v natural solubilizers (1-mogroside V, 3-geniposide, 4-paeoniflorin, and 8-rebaudioside A) as complexing agents, respectively, are shown in FIG. 5. CPT9 was camptothecin dissolved in water without any solubilizers (control). The HPLC system included 600 pump, 717 autosampler, and 2996 PDA. Chromatograms were generated using a Prevail C18 column (2.1× 150 mm, 3 μm) and a mobile phase of ACN (32): 0.02% HCOOH—H20 (68) at a flow rate of 0.4 mL/min, injection volume of 1 μL, UV detection wavelength of 368 nm, and column temperature of 30° C. Camptothecin concentration was determined using a standard calibration curve with camptothecin standard solutions of 14, 70, and 140 μg/mL. The chromatograms above were generated at 368 nm UV showing elution of camptothecin at 7.3 min, the peak areas of which were used for quantification of camptothecin. The contents of astragaloside and steviol monoside in solutions were less than 10%, as judged by their precipitations in the water solutions.

In the presence of 10% w/v of mogroside V (1), geniposide (3), paeoniflorin (4), rebaudioside A or (8), the water solutions contained 18 μg/mL, 25 μg/mL, 54 μg/mL, or 48 μg/mL camptothecin, respectively (FIG. 5). The control water solution had no detectable level of camptothecin.

Figure 6:
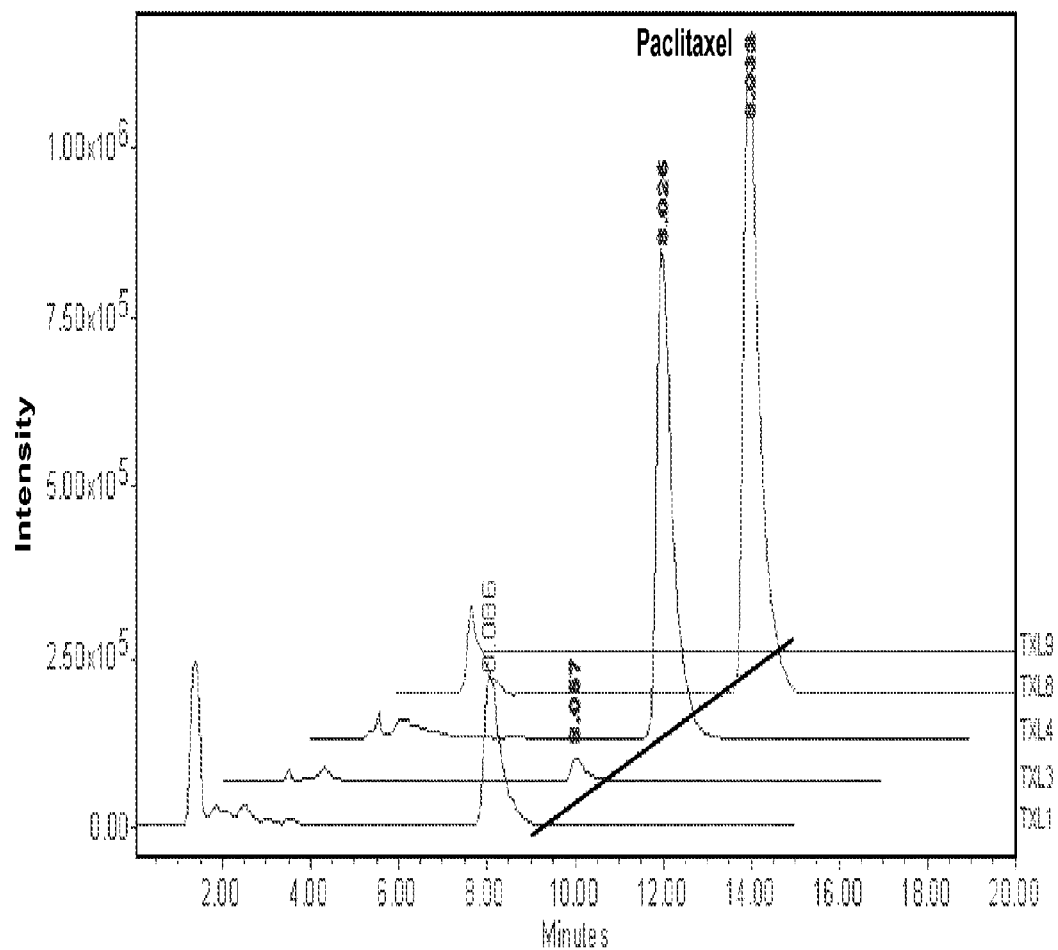
FIG. 6 illustrates the results of high performance liquid chromatography indicating the amount of dissolved paclitaxel in five solutions: TXL1, 10% mogroside V; TXL3, 10% geniposide; TXL4, 10% paeoniflorin; TXL8, 10% rebaudioside A; and TXL9, water (control).

Paclitaxel:

Chromatograms of five paclitaxel (Taxol) water solutions. TXL1, TXL3, TXL4, and TXL8 containing 10% w/v natural solubilizers (1-mogroside V, 3-geniposide, 4-paeoniflorin, and 8-rebaudioside A) as complexing agents, respectively, are shown in FIG. 6. TXL9 was taxol dissolved in water without any solubilizers (control). The HPLC-MS (Waters HPLC-MS system with 600 pump, 717 autosampler, 2996 PDA, and an EMD1000 MS detector) chromatograms were generated using a Prevail C18 column (2.1×150 mm, 3 μm) and a mobile phase of 0.25% HCOOH:ACN:MeOH (4:4:2 v/v/v); at a flow rate of 0.40 mL/min, injection volume of 1 μL, UV detection wavelength of 230 nm, and column temperature of 30° C. MS detection was performed with MS-ESI in positive mode and a SIR scan at m/z 854.4. Taxol concentration was determined using a standard calibration curve with taxol standard solutions of 0.02, 0.06, and 0.2 mg/mL. The chromatograms above were generated at SIR scan at m/z 854.4 showing elution of taxol at 8.1 min, the peak areas of which were used for quantification of taxol. The contents of astragaloside and steviol monoside in solutions were less than 10%, as judged by their precipitations in the water solutions In the presence of 10% w/v of mogroside V (1), geniposide (3), paeoniflorin (4), or rebaudioside A (8), the water solutions contained 7 μg/mL, 1 μg/mL, 20 μg/mL, or 26 μg/mL paclitaxel, respectively (FIG. 6). The control water solution had no detectable level of paclitaxel (FIG. 6).

Example 4

Effect of Mogroside V, Astragaloside IV, Geniposide, or Paeoniflorin on the Water Solubility of Tanshinone IIa, Coenzyme Q10, Amphotericin b, Artemisinin, Podophyllotoxin, Silybin, Propofol, and Celecoxib A ten percent water solution w/v of mogroside V (1), astragaloside IV (2), geniposide (3), paeoniflorin (4), or a water control containing no solubilizing agents (5) was each prepared. One set of two milligrams of tanshinone IIA, coenzyme Q10, amphotericin B, artemisinin, podophyllotoxin, silybin, propofol, or celecoxib were each weighed into separate centrifuge tubes, and received 1 mL of one of the solubilizing agent 1, 2, 3, 4, or 5 (control). These water solutions were sonicated at 50° C. for 60 min followed by incubation at 25° C. for 72 hr. These compounds in the solubilized water solutions were filtered by 0.45 μM filters and analyzed on HPLC. Quantification was done by comparing to a standard solution of a known amount in methanol.

Figure 7:
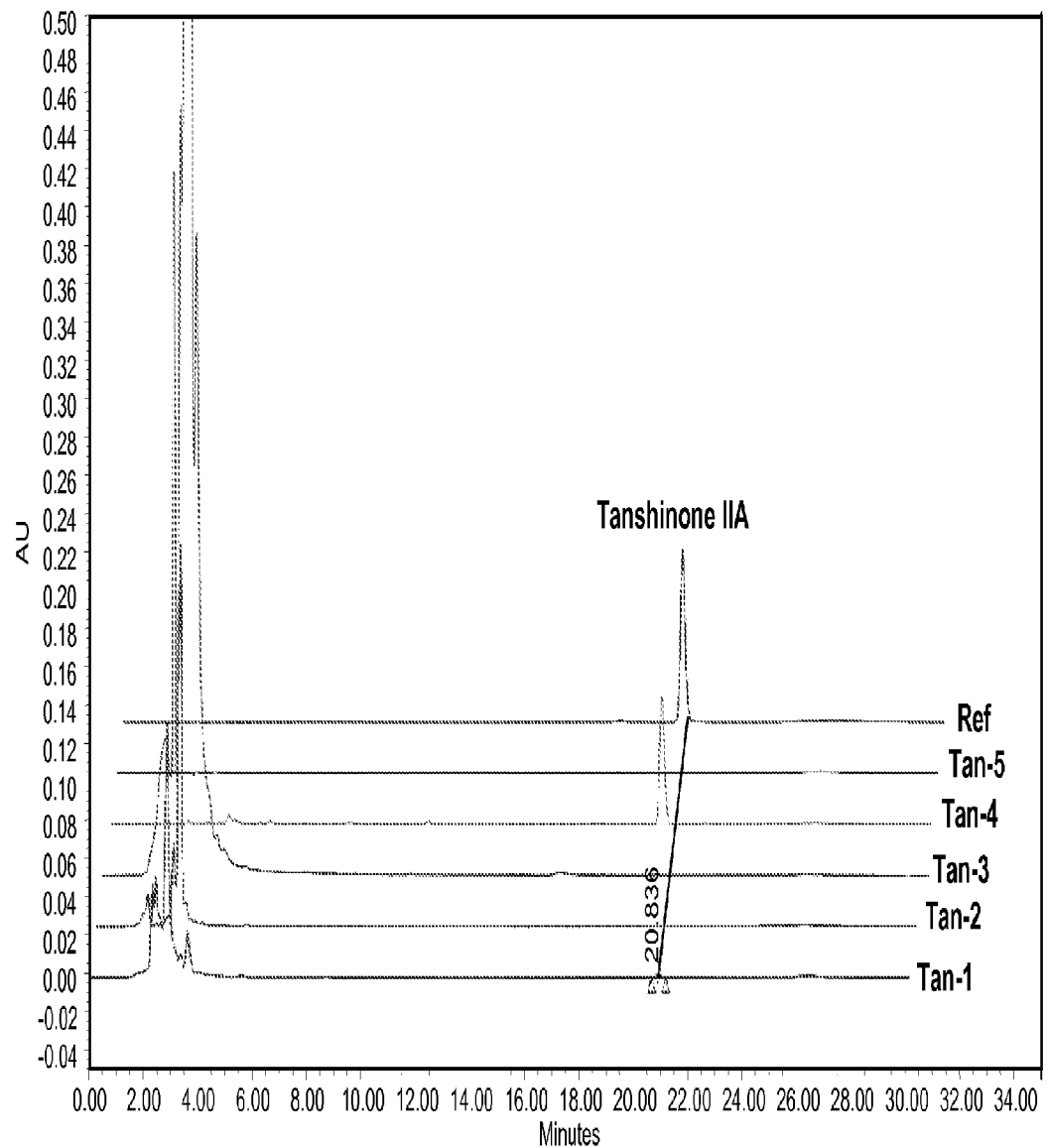
FIG. 7 illustrates the results of high performance liquid chromatography indicating the amount of dissolved tanshinone IIA in six solutions: Tan-1, 10% geniposide; Tan-2, 10% paeoniflorin; Tan-3, 10% mogroside V; Tan-4, 10% astragaloside IV; Tan-5, water (control); and Ref, 30.4 µg/ml tanshinone IIA in methanol (reference standard).

Tanshinone IIA:

Quantitative determination of tanshinone IIA is shown in FIG. 7. All the chromatograms were detected using HPLC at the wavelength of 280 nm. A Luna C18 column (4.6 mm×250 mm, 5 μm) was used for the analyses. The mobile phase consisted of methanol (A) and water (B). Tanshinone IIA was eluted at 20.836 min. Tan-1 is the water solution containing 10% geniposide; Tan-2 is the water solution containing 10% paeoniflorin; Tan-3 is the water solution containing 10% mogroside V; Tan-4 is the water solution containing 10% astragaloside IV; Tan-5 is the water only solution (control); and Ref is the reference standard compound of 30.4 μg/mL in methanol.

In the presence of 10% w/v of mogroside V (1), astragaloside IV (2), geniposide (3), or paeoniflorin (4), the water solutions contained 0.5 μg/mL, 0 μg/mL, 0.1 μg/mL, or 23 μg/mL tanshinone IIA, respectively. The control water solution had no detectable level of tanshinone IIA (FIG. 7).

Coenzyme Q10:

In the presence of 10% w/v of mogroside V (1), astragaloside IV (2), geniposide (3), or paeoniflorin (4), none of the water solutions contained any detectable coenzyme Q10. The control water solution had no detectable level of coenzyme Q10 (Data not shown).

Figure 8:
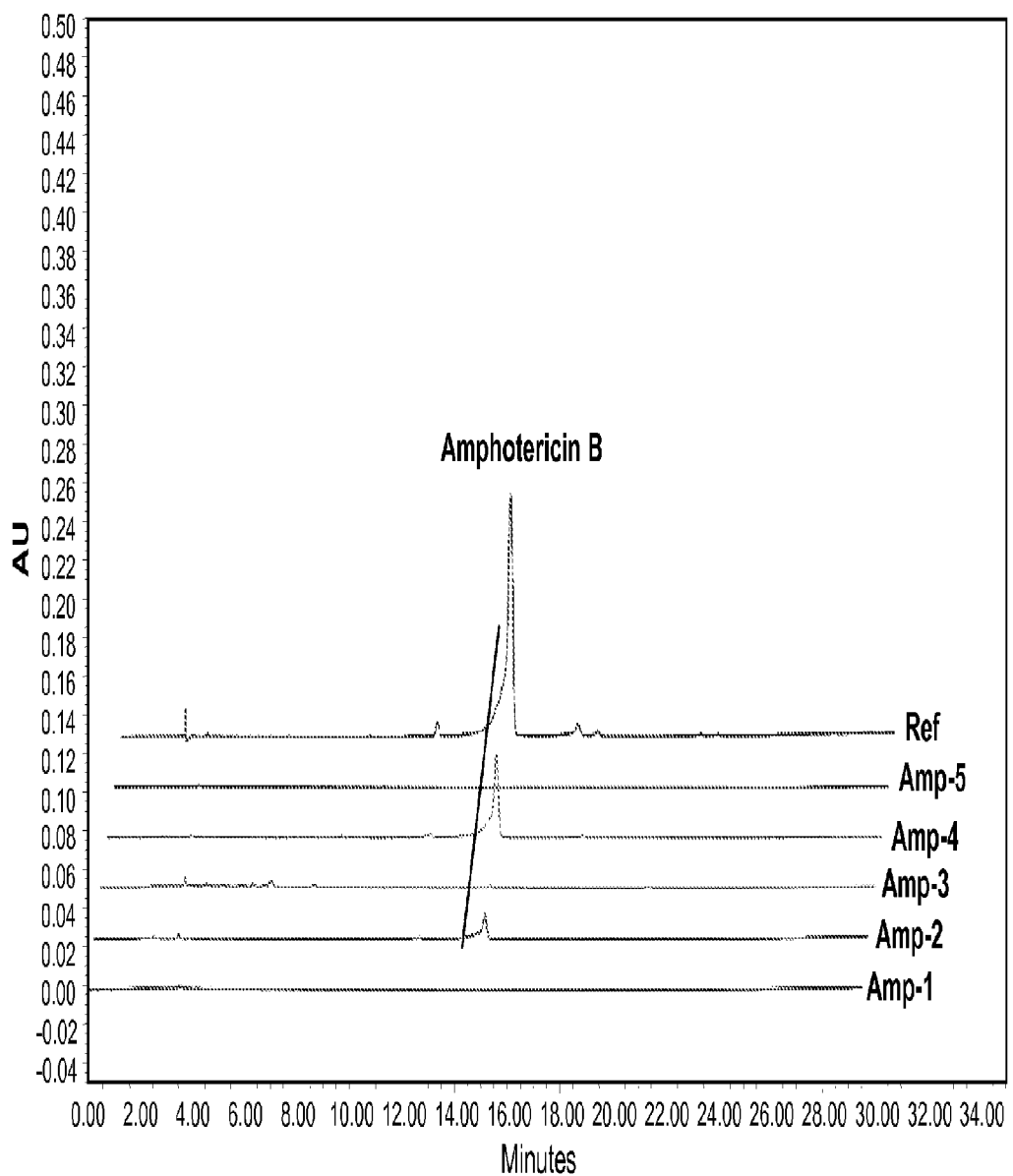
FIG. 8 illustrates the results of high performance liquid chromatography indicating the amount of dissolved amphotericin B in six solutions: Amp-1, 10% geniposide; Amp-2, 10% paeoniflorin; Amp-3, 10% mogroside V; Amp-4, 10% astragaloside IV; Amp-5, water (control); and Ref, 55 µg/ml amphotericin B in methanol (reference standard).

Amphotericin B:

Quantitative determination of amphotericin B is shown in FIG. 8. All the chromatograms were detected at the wavelength of 410 nm. A Luna C18 column (4.6 mm×250 mm, 5 μm) was used for the analyses. The mobile phase consisted of methanol (A) and water (B). Amphotericin B was eluted at 15.000 min. Amp-1 is the water solution containing 10% geniposide; Amp-2 is the water solution containing 10% paeoniflorin; Amp-3 is the water solution containing 10% mogroside V; Amp-4 is the water solution containing 10% astragaloside IV; Amp-5 is the water only solution (control); and Ref is the reference standard compound of 55 μg/mL in methanol.

In the presence of 10% w/v of mogroside V (1), astragaloside IV (2), geniposide (3), or paeoniflorin (4), the water solutions contained 6 μg/mL, 0 μg/mL, 0.2 μg/mL, or 19 μg/mL amphotericin B, respectively. The control water solution had no detectable level of amphotericin B (FIG. 8).

Figure 9:
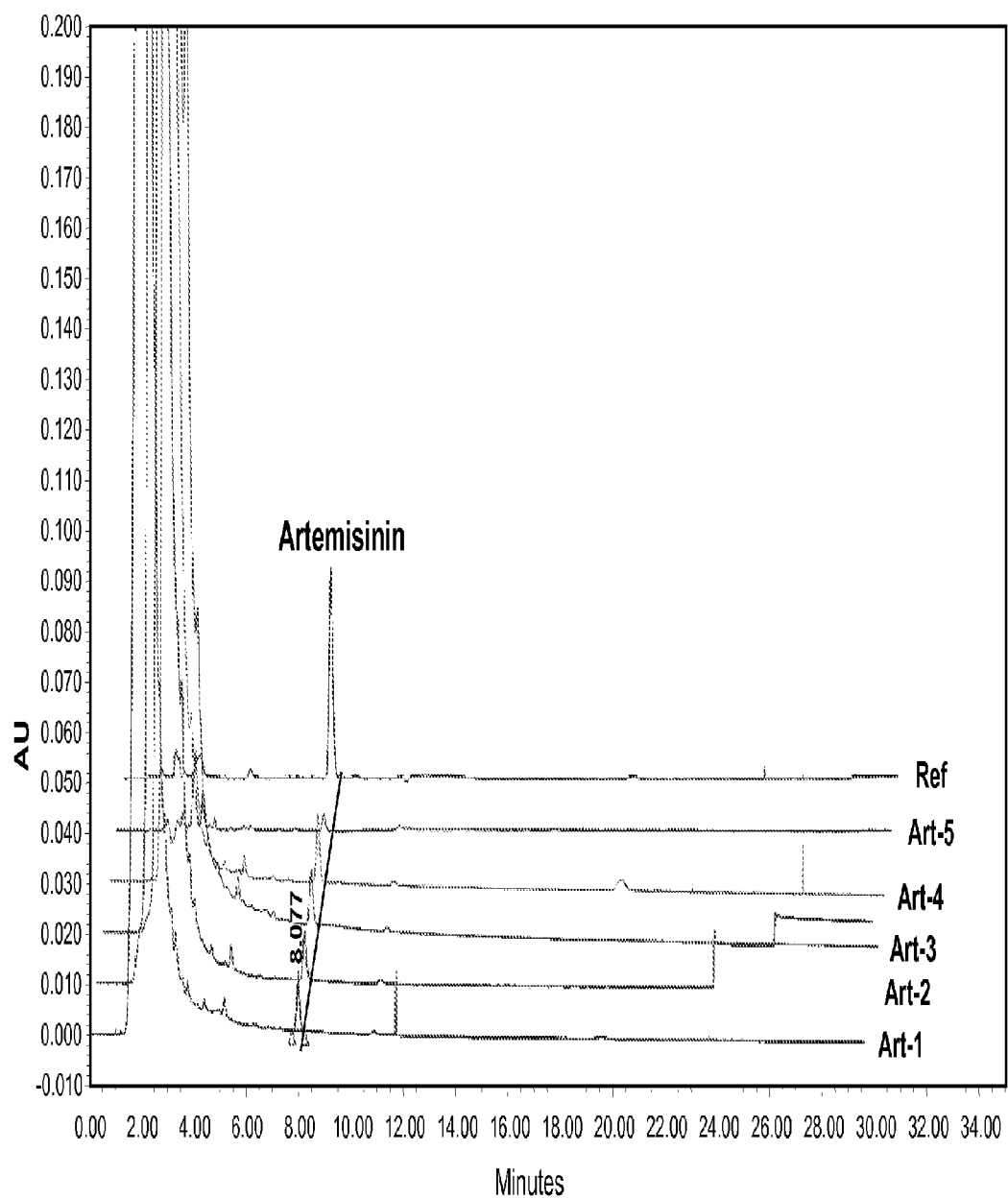
FIG. 9 illustrates the results of high performance liquid chromatography indicating the amount of dissolved artemisinin in six solutions: Art-1, 10% geniposide; Art-2, 10% paeoniflorin; Art-3, 10% mogroside V; Art-4, 10% astragaloside IV; Art-5, water (control); and Ref, 730 µg/ml artemisinin in methanol (reference standard).

Artemisinin:

Quantitative determination of artemisinin is shown in FIG. 9. All the chromatograms were detected at the wavelength of 205 nm. A Luna C18 column (4.6 mm×250 mm, 5 μm) was used for the analyses. The mobile phase consisted of methanol (A) and water (B). Artemisinin was eluted at 8.077 min. Art-1 is the water solution containing 10% geniposide; Art-2 is the water solution containing 10% paeoniflorin; Art-3 is the water solution containing 10% mogroside V; Art-4 is the water solution containing 10% astragaloside IV; Art-5 is the water only solution (control); and Ref is the reference standard compound of 730 μg/mL in methanol.

In the presence of 10% w/v of mogroside V (1), astragaloside IV (2), geniposide (3), or paeoniflorin (4), the water solutions contained 148 μg/mL, 0 μg/mL, 146 μg/mL, or 218 μg/mL artemisinin, respectively. The control water solution had 53 μg/mL of artemisinin (FIG. 9).

Figure 10:
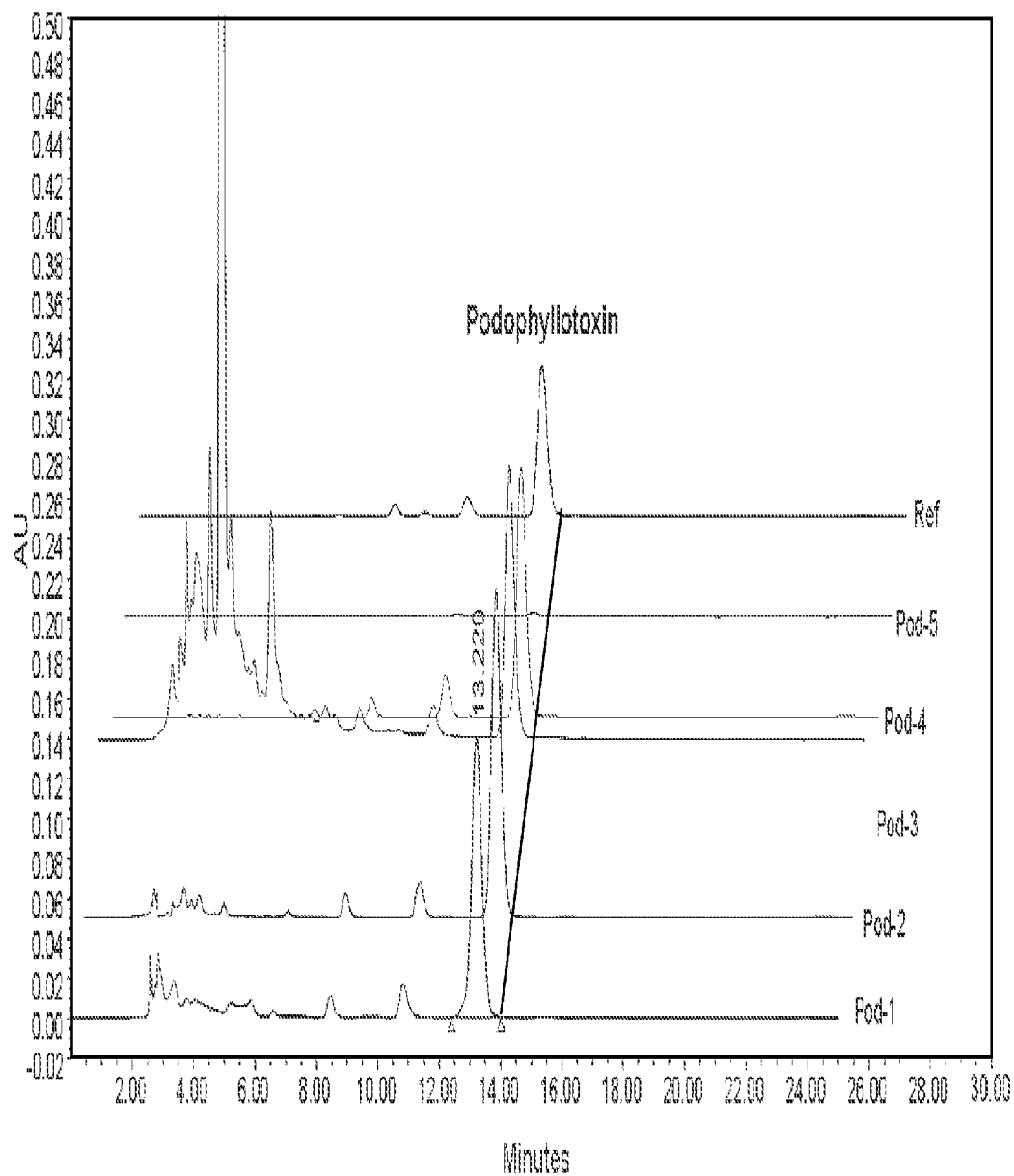
FIG. 10 illustrates the results of high performance liquid chromatography indicating the amount of dissolved podophyllotoxin in six solutions: Pod-1, 10% geniposide; Pod-2, 10% paeoniflorin; Pod-3, 10% mogroside V; Pod-4, 10% astragaloside IV; Pod-5, water (control); and Ref, 370 µg/ml podophyllotoxin in methanol (reference standard).

Podophyllotoxin:

Quantitative determination of podophyllotoxin is shown in FIG. 10. All the chromatograms were detected at the wavelength of 290 nm. A Luna C18 column (4.6 mm×250 mm, 5 μm) was used for the analyses. The mobile phase consisted of methanol (A) and water (B). Podophyllotoxin was eluted at 13.220 min. Pod-1 is the water solution containing 10% geniposide; Pod-2 is the water solution containing 10% paeoniflorin; Pod-3 is the water solution containing 10% mogroside V; Pod-4 is the water solution containing 10% astragaloside IV; Pod-5 is the water only solution (control); and Ref is the reference standard compound of 370 μg/mL in methanol.

In the presence of 10% w/v of mogroside V (1), astragaloside IV (2), geniposide (3), or paeoniflorin (4), the water solutions contained 747 μg/mL, 0 μg/mL, 644 μg/mL, or 586

μg/mL podophyllotoxin, respectively. The control water solution had 53 μg/mL of podophyllotoxin (FIG. 10).

Figure 11:
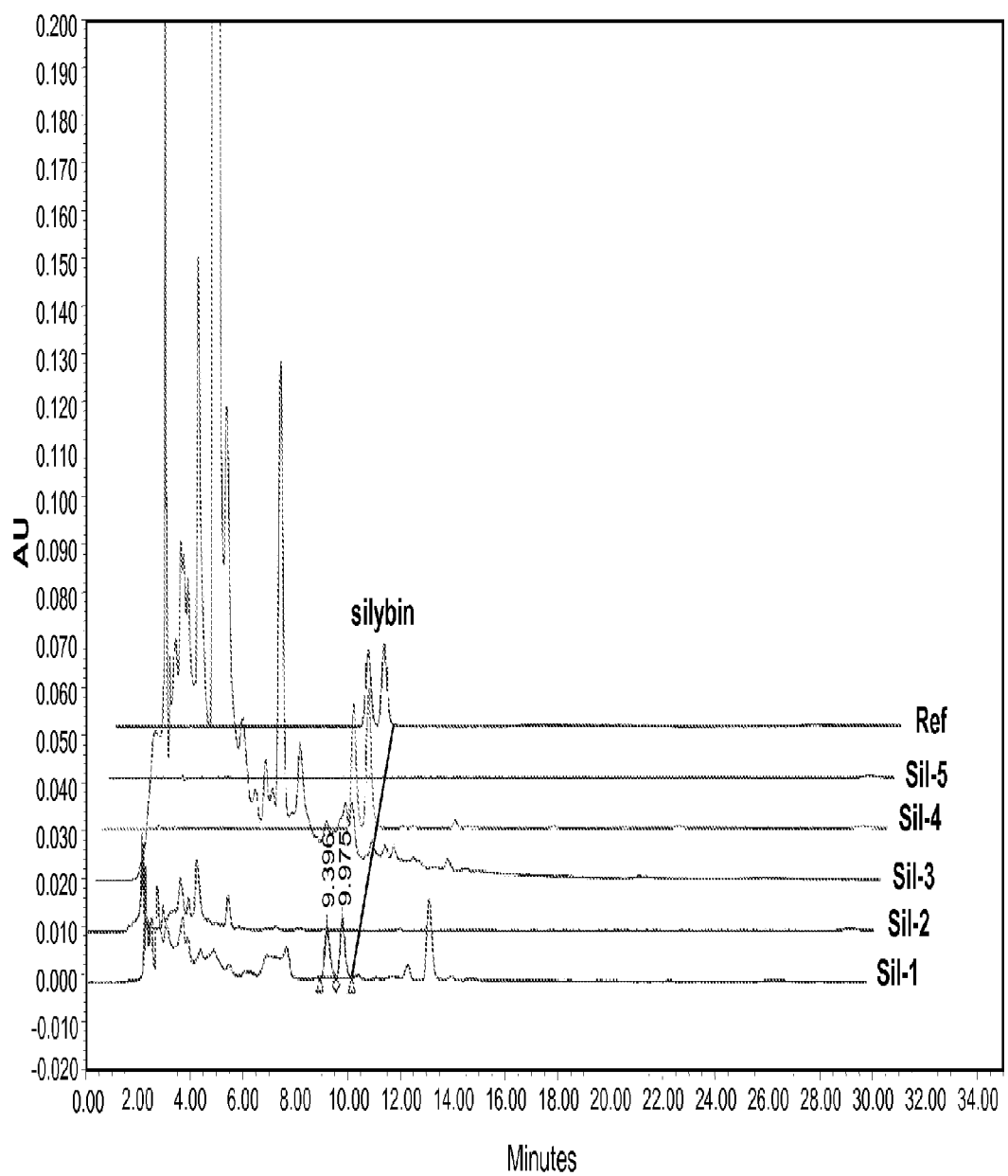
FIG. 11 illustrates the results of high performance liquid chromatography indicating the amount of dissolved silybin in six solutions: Sil-1, 10% geniposide; Sil-2, 10% paeoniflorin; Sil-3, 10% mogroside V; Sil-4, 10% astragaloside IV; Sil-5, water (control); and Ref, 26 µg/ml silybin in methanol (reference standard).

Silybin:

Quantitative determination of silybin is shown FIG. 11. All the chromatograms were detected at the wavelength of 288 nm. A Luna C18 column (4.6 mm×250 mm, 5 μm) was used for the analyses. The mobile phase consisted of methanol (A) and water (B). Podophyllotoxin was eluted at 9.975 min. Sil-1 is the water solution containing 10% geniposide; Sil-2 is the water solution containing 10% paeoniflorin; Sil-3 is the water solution containing 10% mogroside V; Sil-4 is the water solution containing 10% astragaloside IV; Sil-5 is the water only solution (control); and Ref is the reference standard compound of 26 μg/mL in methanol.

In the presence of 10% w/v of mogroside V (1), astragaloside IV (2), geniposide (3), or paeoniflorin (4), the water solutions contained 18 μg/mL, 0 μg/mL, 16 μg/mL, or 37 μg/mL silybin, respectively. The control water solution had no detectable level of silybin (FIG. 11).

Figure 12:
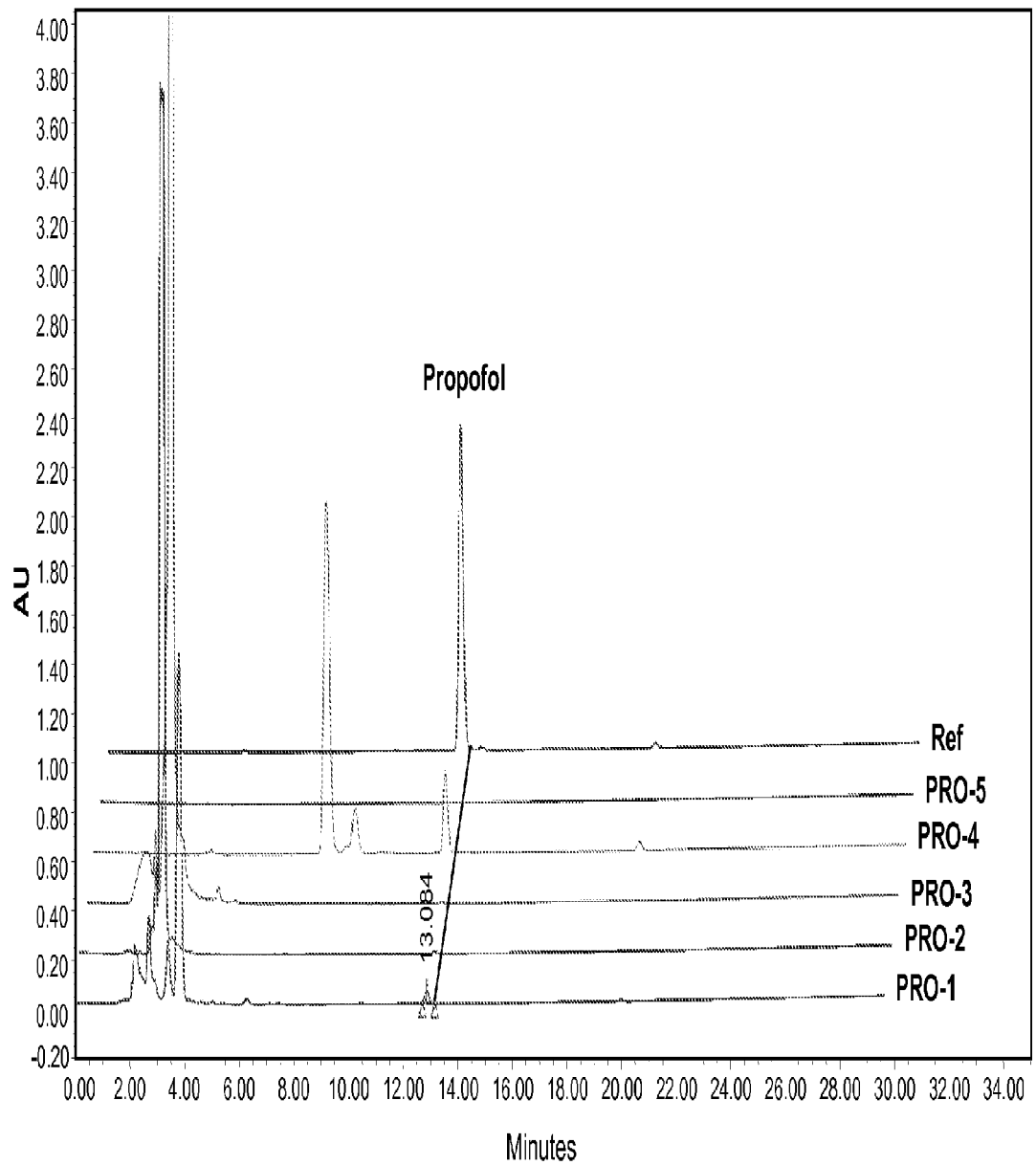
FIG. 12 illustrates the results of high performance liquid chromatography indicating the amount of dissolved propofol in six solutions: PRO-1, 10% geniposide; PRO-2, 10% paeoniflorin; PRO-3, 10% mogroside V; PRO-4, 10% astragaloside IV; PRO-5, water (control); and Ref, 702 µg/ml propofol in methanol (reference standard).

Propofol:

Quantitative determination of propofol is shown in FIG. 12. All the chromatograms were detected at the wavelength of 270 nm. A Luna C18 column (4.6 mm×250 mm, 5 μm) was used for the analyses. The mobile phase consisted of methanol (A) and water (B). Propofol was eluted at 13.084 min. PRO-1 is the water solution containing 10% geniposide; PRO-2 is the water solution containing 10% paeoniflorin; PRO-3 is the water solution containing 10% mogroside V; PRO-4 is the water solution containing 10% astragaloside IV; PRO-5 is the water only solution (control); and Ref is the reference standard compound of 702 μg/mL in methanol.

In the presence of 10% w/v of mogroside V (1), astragaloside IV (2), geniposide (3), or paeoniflorin (4), the water solutions contained 56 μg/mL, 0 μg/mL, 7 μg/mL, or 349 μg/mL propofol, respectively. The control water solution had no detectable level of propofol (FIG. 12).

Figure 13:
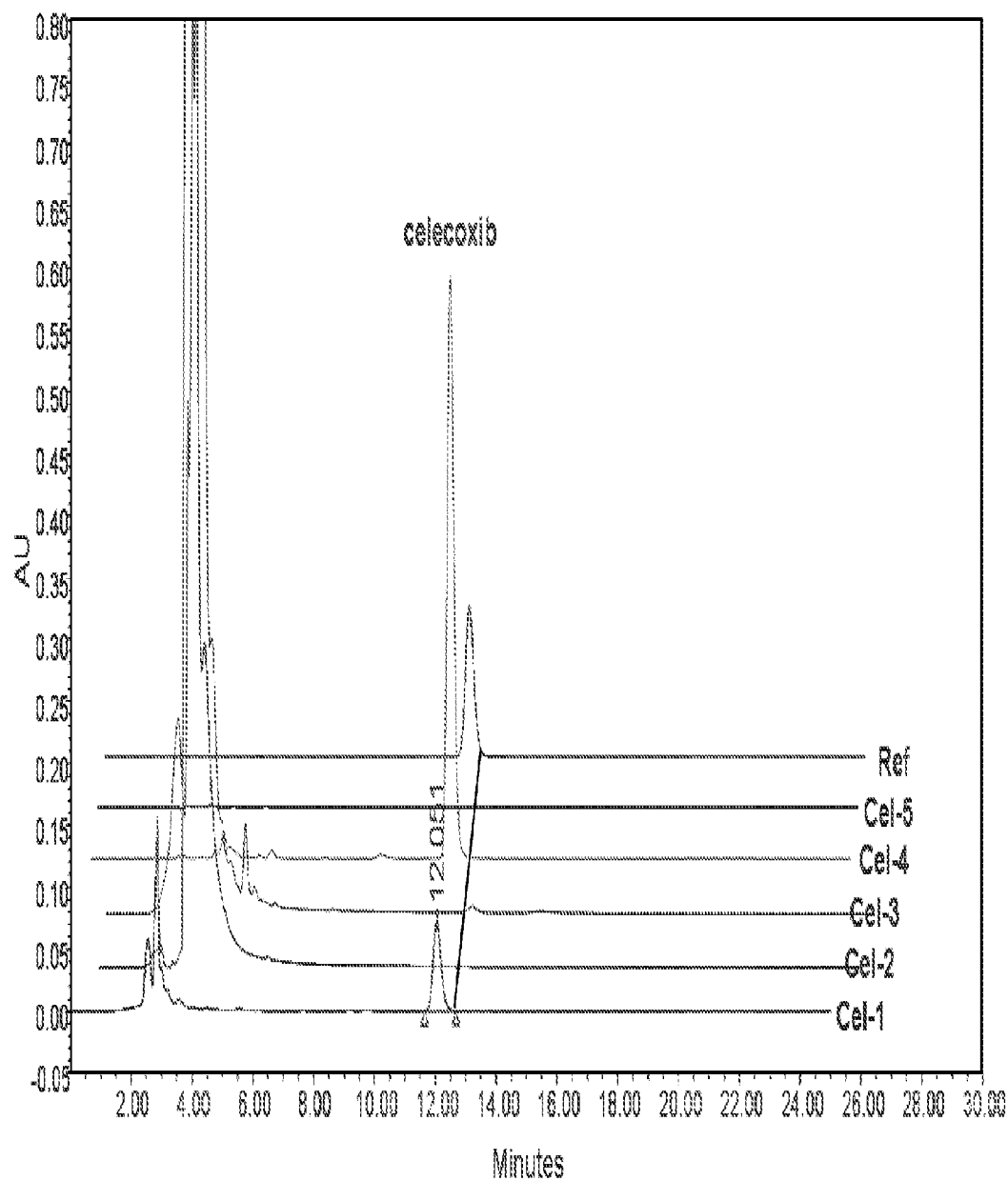
FIG. 13 illustrates the results of high performance liquid chromatography indicating the amount of dissolved celecoxib in six solutions: Cel-1, 10% geniposide; Cel-2, 10% paeoniflorin; Cel-3, 10% mogroside V; Cel-4, 10% astragaloside IV; Cel-5, water (control); and Ref, 84 µg/ml celecoxib in methanol (reference standard).

Celecoxib:

Quantitative determination of celecoxib in FIG. 13. All the chromatograms were detected at the wavelength of 254 nm. A Luna C18 column (4.6 mm×250 mm, 5 μm) was used for the analyses. The mobile phase consisted of methanol (A) and water (B). Podophyllotoxin was eluted at 12.051 min. Cel-1 is the water solution containing 10% geniposide; Cel-2 is the water solution containing 10% paeoniflorin; Cel-3 is the water solution containing 10% mogroside V; Cel-4 is the water solution containing 10% astragaloside IV; Cel-5 is the water only solution (control); and Ref is the reference standard compound of 84 μg/mL in methanol.

In the presence of 10% w/v of mogroside V (1), astragaloside IV (2), geniposide (3), or paeoniflorin (4), the water solutions contained 47 μg/mL, 0 μg/mL, 3 μg/mL, or 253 μg/mL celecoxib, respectively. The control water solution had no detectable level of celecoxib (FIG. 13).

Example 5

Effect of Geniposide, Paeoniflorin, Mogroside V, Astragaloside IV, Rubusoside, Steviol Monoside, Stevioside, and Rebaudioside A on the Water Solubility of Clofazimine, Digoxin, Oleandrin, Nifedipine, and Amiodarone Ten percent w/v of mogroside V (1), astragaloside IV (2), geniposide (3), paeoniflorin (4), rubusoside (5), steviol monoside (6), stevioside (7), rebaudioside A (8) or a water control containing no solubilizing agents (9) water solutions was each prepared. One set of two milligrams of clofazimine, digoxin, oleandrin, nifedipine, or amiodarone were each weighed into separate centrifuge tubes, and received 1 mL of one of the solubilizing agent 1, 2, 3, 4, 5, 6, 7, 8, or 9 (control). These water solutions were sonicated at 50° C. for 60 min followed by incubation at 25° C. for 72 hr. These compounds in the solubilized water solutions were filtered by 0.45 μM filters and analyzed on HPLC. Quantification was done by comparing to a standard solution of a known amount in methanol.

Clofazimine:

Quantitative determination of clofazimine is shown in FIG. 14. All the chromatograms were detected at the wavelength of 289 nm. A Luna C18 column (4.6 mm×250 mm, 5 μm) was used for the analyses. The mobile phase consisted of methanol (A) and water (B). Clofazimine was eluted at 15.000 min. C1 is the water solution containing 10% mogroside V; C2 is the water solution containing 10% astragaloside IV; C3 is the water solution containing 10% geniposide; C4 is the water solution containing 10% paeoniflorin; C5 is the water solution containing 10% rubusoside; C6 is the water solution containing 10% steviol monoside; C7 is the water solution containing 10% stevioside; C8 is the water solution containing 10% rebaudioside A; C9 is the water only solution (control); and Ref is the reference standard compound of 160 μg/mL in methanol.

In the presence of 10% w/v of mogroside V (1), astragaloside IV (2), geniposide (3), or paeoniflorin (4), rubusoside (5), steviol monoside (6), stevioside (7), or rebaudioside A (8), the water solutions contained 58 μg/mL, 0.4 μg/mL, 48 μg/mL, 565 μg/mL, 132 μg/mL, 0 μg/mL, 64 μg/mL, or 109 μg/mL clofazimine, respectively. The control water solution had 7.6 μg/mL of clofazimine (FIG. 14).

Digoxin:

Quantitative determination of digoxin is shown in FIG. 15. All the chromatograms were detected at the wavelength of 230 nm. A Luna C18 column (4.6 mm×250 mm, 5 μm) was used for the analyses. The mobile phase consisted of methanol (A) and water (B). Digoxin was eluted at 16.927 min. D1 is the water solution containing 10% mogroside V; D2 is the water solution containing 10% astragaloside IV; D3 is the water solution containing 10% geniposide; D4 is the water solution containing 10% paeoniflorin; D5 is the water solution containing 10% rubusoside; D6 is the water solution containing 10% steviol monoside; D7 is the water solution containing 10% stevioside; D8 is the water solution containing 10% rebaudioside A; D9 is the water only solution (control); and Ref is the reference standard compound of 388 μg/mL in methanol In the presence of 10% w/v of mogroside V (1), astragaloside IV (2), geniposide (3), or paeoniflorin (4), rubusoside (5), steviol monoside (6), stevioside (7), or rebaudioside A (8), the water solutions contained 35 μg/mL, 18 μg/mL, 26 μg/mL, 38 μg/mL, 48 μg/mL, 10 μg/mL, 30 μg/mL, or 32 μg/mL digoxin, respectively. The control water solution had 19 μg/mL of digoxin (FIG. 15).

Oleandrin:

Quantitative determination of oleandrin is shown in FIG. 16. All the chromatograms were detected at the wavelength of 230 nm. A Luna C18 column (4.6 mm×250 mm, 5 μm) was used for the analyses. The mobile phase consisted of methanol (A) and water (B). Oleandrin was eluted at 18.624 min. O1 is the water solution containing 10% mogroside V; O2 is the water solution containing 10% astragaloside IV; O3 is the water solution containing 10% geniposide; O4 is the water solution containing 10% paeoniflorin; O5 is the water solution containing 10% rubusoside; O6 is the water solution containing 10% steviol monoside; O7 is the water solution containing 10% stevioside; O8 is the water solution containing 10% rebaudioside A; O9 is the water only solution (control); and Ref is the reference standard compound of 260 µg/mL in methanol In the presence of 10% w/v of mogroside V (1), astragaloside IV (2), geniposide (3), or paeoniflorin (4), rubusoside (5), steviol monoside (6), stevioside (7), or rebaudioside A (8), the water solutions contained 47 µg/mL, 5 µg/mL, 28 µg/mL, 42 µg/mL, 123 µg/mL, 7 µg/mL, 74 µg/mL, or 67 µg/mL oleandrin, respectively. The control water solution had 3 µg/mL of oleandrin (FIG. 16).

Nifedipine:

Quantitative determination of nifedipine is shown in FIG. 17. All the chromatograms were detected at the wavelength of 235 nm. A Luna C18 column (4.6 mm×250 mm, 5 µm) was used for the analyses. The mobile phase consisted of methanol (A) and water (B). Nifedipine was eluted at 20.871 min. N1 is the water solution containing 10% mogroside V; N2 is the water solution containing 10% astragaloside IV; N3 is the water solution containing 10% geniposide; N4 is the water solution containing 10% paeoniflorin; N5 is the water solution containing 10% rubusoside; N6 is the water solution containing 10% steviol monoside; N7 is the water solution containing 10% stevioside; N8 is the water solution containing 10% rebaudioside A; N9 is the water only solution (control); and Ref is the reference standard compound of 240 µg/mL in methanol.

In the presence of 10% w/v of mogroside V (1), astragaloside IV (2), geniposide (3), or paeoniflorin (4), rubusoside (5), steviol monoside (6), stevioside (7), or rebaudioside A (8), the water solutions contained 55 µg/mL, 0 µg/mL, 39 µg/mL, 49 µg/mL, 286 µg/mL, 0 µg/mL, 468 µg/mL, or 203 µg/mL nifedipine, respectively. The control water solution had no detectable level of nifedipine (FIG. 17).

Amiodarone:

Quantitative determination of amiodarone is shown in FIG. 18. All the chromatograms were detected at the wavelength of 242 nm. A Luna C18 column (4.6 mm×250 mm, 5 µm) was used for the analyses. The mobile phase consisted of methanol (A) and water (B). Amiodarone was eluted at 18.311 min. A1 is the water solution containing 10% mogroside V; A2 is the water solution containing 10% astragaloside IV; A3 is the water solution containing 10% geniposide; A4 is the water solution containing 10% paeoniflorin; A5 is the water solution containing 10% rubusoside; A6 is the water solution containing 10% steviol monoside; A7 is the water solution containing 10% stevioside; A8 is the water solution containing 10% rebaudioside A; A9 is the water only solution (control); and Ref is the reference standard compound of 104 µg/mL in methanol.

In the presence of 10% w/v of mogroside V (1), astragaloside IV (2), geniposide (3), or paeoniflorin (4), rubusoside (5), steviol monoside (6), stevioside (7), or rebaudioside A (8), the water solutions contained 238 µg/mL, 164 µg/mL, 236 µg/mL, 251 µg/mL, 249 µg/mL, 0 µg/mL, 201 µg/mL, or 271 µg/mL amiodarone, respectively. The control water solution had 107 µg/mL of amiodarone (FIG. 18).

Example 6

Effect of the Combination of a Monoterpene Glycoside, a Diterpene Glycoside, and a Triterpene Glycoside on the Water Solubility of Curcumin, Paclitaxel, Camptothecin, Tanshinone IIA, Digoxin, Itraconazole, and Celecoxib Ten percent w/v of the combination of solubilizers consisting of a monoterpene glycoside (paeoniflorin), a di-terpene glycoside (rubusoside), and a tri-terpene glycoside (mogroside V) at 1:1:1 w/w/w ratio or a water control containing no solubilizing agents water solutions will be each prepared. One set of two milligrams of curcumin, paclitaxel, camptothecin, tanshinone IIA, digoxin, itraconazole, and celecoxib is each weighed into separate centrifuge tubes, and received 1 mL of either the 10% combinational solubilizing agents or a water control. These water solutions are sonicated at 50° C. for 60 min followed by incubation at 25° C. for 72 hr. These compounds in the solubilized water solutions are filtered by 0.45 µM filters and analyzed on HPLC. Quantification is done by comparing to a standard solution of a known amount in methanol. It is expected that the combination of a monoterpene glycoside (paeoniflorin), a di-terpene glycoside (rubusoside), and a tri-terpene glycoside (mogroside V) at 1:1:1 w/w/w ratio will increase the solubility of curcumin, paclitaxel, camptothecin, tanshinone IIA, digoxin, itraconazole, and celecoxib.

The complete disclosures of all references cited in this specification are hereby incorporated by reference, including U.S. provisional patent application Ser. No. 61/219,973 and International Application No. PCT/US2009/040324, published as WO2009/126950. In the event of an otherwise irreconcilable conflict, however, the present specification shall control.

What is claimed:

1. A method for enhancing the solubility of an organic compound which is insoluble or sparingly soluble in water, said method comprising mixing said organic compound with water and with a concentration of mogroside V sufficient to increase the solubility of the organic compound in water by a factor of 2 or more above what the solubility would be in water without the mogroside V; wherein the organic compound is selected from the group consisting of diterpenes, quinoline alkaloids, phenylalanine-derived alkaloids, hydrolysable tannins, flavonoids, curcuminoids, phenols, polymeric macrolides, cyclic peptides, sesquiterpene lactones, lignans, flavonolignans, lipids, azoles, dihydropyridines, amiodarones, and riminophenazines, wherein the concentration of mogroside V is from about 1% to about 40% weight/volume.

2. The method of claim 1, wherein the organic compound is selected from the group consisting of curcumin, camptothecin, paclitaxel, amphotericin B, artemisinin, podophyllotoxin, silybin, propofol, celecoxib, clofazimine, oleandrin, nifedipine, and amiodarone.

3. The method of claim 1, wherein the concentration of mogroside V is about 10% w/v.

4. The method of claim 1, additionally comprising one or more solubilizing compounds to assist in solubilizing the organic compound, wherein said solubilizing compound is selected from the group consisting of paeoniflorin, cyclodextrin, geniposide, rubusoside, steviol monoside, stevioside, and rebaudioside A.

5. A method for enhancing the solubility of an organic compound which is insoluble or sparingly soluble in water, said method comprising mixing said compound with water and with geniposide in a concentration sufficient to increase the solubility of the organic compound in water by a factor of 2 or more above what the solubility would be in water without the geniposide; wherein the organic compound is selected from the group consisting of quinoline alkaloids, phenylalanine-derived alkaloids, hydrolysable tannins, flavonoids, curcuminoids, phenols, cyclic peptides, sesquiterpene lactones, lignans, flavonolignans, lipids, azoles, dihydropyridines, amiodarones, and riminophenazines, wherein the concentration of geniposide is from about 1% to about 40% weight/volume.

6. The method of claim 5, wherein the organic compound is selected from the group consisting of curcumin, camptothecin, artemisinin, podophyllotoxin, silybin, propofol, celecoxib, clofazimine, oleandrin, nifedipine, and amiodarone.

7. The method of claim 5, wherein the concentration of geniposide is about 10% w/v.

8. The method of claim 5, additionally comprising one or more solubilizing compounds to assist in solubilizing the organic compound, wherein said solubilizing compound is selected from the group consisting of mogroside V, cyclodextrin, paeoniflorin, rubusoside, steviol monoside, stevioside, and rebaudioside A.

9. A method for enhancing the solubility of an organic compound which is insoluble or sparingly soluble in water, said method comprising mixing said organic compound with water and with a concentration of rubusoside sufficient to increase the solubility of the organic compound in water by a factor of 2 or more above what the solubility would be in water without the rubusoside; wherein the organic compound is selected from the group consisting of cardiac glycosides, dihydropyridines, amiodarones, and riminophenazines, wherein the concentration of rubusoside is from about 1% to about 40% weight/volume.

10. The method of claim 9, wherein the organic compound is selected from the group consisting of clofazimine, digoxin, oleandrin, nifedipine, and amiodarone.

11. The method of claim 9, wherein the concentration of rubusoside is about 10% w/v.

12. The method of claim 9, additionally comprising one or more solubilizing compounds to assist in solubilizing the organic compound, wherein said solubilizing compound is selected from the group consisting of mogroside V, cyclodextrin, paeoniflorin, geniposide, steviol monoside, stevioside, and rebaudioside A.

13. A method for enhancing the solubility of an organic compound which is insoluble or sparingly soluble in water, said method comprising mixing said compound with water and with a concentration of stevioside sufficient to increase the solubility of the compound in water by a factor of 2 or more above what the solubility would be in water without the stevioside; wherein the organic compound is selected from the group consisting of phenazines and riminophenazines, wherein the concentration of stevioside is from about 1% to about 40% weight/volume.

14. The method of claim 13, wherein the organic compound is selected from the group consisting of clofazimine, oleandrin, and nifedipine.

15. The method of claim 13, wherein the concentration of stevioside is about 10% w/v.

16. The method of claim 13, additionally comprising one or more solubilizing compounds to assist in solubilizing the organic compound, wherein said solubilizing compound is selected from the group consisting of mogroside V, cyclodextrin, paeoniflorin, geniposide, steviol monoside, rubusoside, and rebaudioside A.

17. A method for enhancing the solubility of an organic compound which is insoluble or sparingly soluble in water, said method comprising mixing said compound with water and with a concentration of rebaudioside A sufficient to increase the solubility of the compound in water by a factor of 2 or more above what the solubility would be in water without the rebaudioside A; wherein the organic compound is selected from the group consisting of phenazines, dihydropyridines, amiodarones, and riminophenazines, wherein the concentration of rebaudioside A is from about 1% to about 40% weight/volume.

18. The method of claim 17, wherein the organic compound is selected from the group consisting of clofazimine, oleandrin, nifedipine, and amiodarone.

19. The method of claim 17, wherein the concentration of rebaudioside A is about 10% w/v.

20. The method of claim 17, additionally comprising one or more solubilizing compounds to assist in solubilizing the organic compound, wherein said solubilizing compound is selected from the group consisting of mogroside V, cyclodextrin, paeoniflorin, geniposide, steviol monoside, stevioside, and rubusoside.

21. A composition comprising an organic compound having low solubility in water, and mogroside V; wherein the organic compound is selected from the group consisting of diterpenes, quinoline alkaloids, phenylalanine-derived alkaloids, hydrolysable tannins, flavonoids, curcuminoids, phenols, macrolides, cyclic peptides, sesquiterpene lactones, lignans, flavonolignans, lipids, azoles, dihydropyridines, amiodarones, and riminophenazines; and wherein the concentration of said mogroside V in the composition is sufficient to increase the solubility of said organic compound in water by a factor of 2 or more above what the solubility would be in an otherwise identical composition lacking said mogroside V, and wherein the concentration of mogroside V is from about 1% to about 40% weight/volume.

22. The composition of claim 21, wherein the organic compound is selected from the group consisting of curcumin, camptothecin, paclitaxel, amphotericin B, artemisinin, podophyllotoxin, silybin, propofol, celecoxib, clofazimine, oleandrin, nifedipine, and amiodarone.

23. The composition of claim 21, additionally comprising one or more solubilizing compound to assist in solubilizing the organic compound, wherein said solubilizing compound is selected from the group consisting of paeoniflorin, cyclodextrin, geniposide, rubusoside, steviol monoside, stevioside, and rebaudioside A.

24. The composition of claim 21, additionally comprising one or more pharmaceutical agents selected from the group consisting of complexing agents, cosolvents, surfactants, emulsifiers, liposomes and nanoparticles.

25. A composition comprising an organic compound having low solubility in water, and geniposide; wherein the organic compound is selected from the group consisting of quinoline alkaloids, phenylalanine-derived alkaloids, hydrolysable tannins, flavonoids, curcuminoids, phenols, cyclic peptides, sesquiterpene lactones, lignans, flavonolignans, lipids, azoles, dihydropyridines, amiodarones, and riminophenazines; and wherein the concentration of said geniposide in the composition is sufficient to increase the solubility of said organic compound in water by a factor of 2 or more above what the solubility would be in an otherwise identical composition lacking said geniposide, and wherein the concentration of geniposide is from about 1% to about 40% weight/volume.

26. The composition of claim 25, wherein the organic compound is selected from the group consisting of curcumin, camptothecin, artemisinin, podophyllotoxin, silybin, propofol, celecoxib, clofazimine, oleandrin, nifedipine, and amiodarone.

27. The composition of claim 25, additionally comprising additionally comprising one or more solubilizing compound to assist in solubilizing the organic compound, wherein said solubilizing compound is selected from the group consisting of mogroside V, cyclodextrin, paeoniflorin, rubusoside, steviol monoside, stevioside, and rebaudioside A.

28. The composition of claim 25, additionally comprising one or more pharmaceutical agents selected from the group consisting of complexing agents, cosolvents, surfactants, emulsifiers, liposomes and nanoparticles.

29. A composition comprising an organic compound having low solubility in water, and rubusoside; wherein the organic compound is selected from the group consisting of cardiac glycosides, dihydropyridines, amiodarones, and riminophenazines; and wherein the concentration of said rubusoside in the composition is sufficient to increase the solubility of said organic compound in water by a factor of 2 or more above what the solubility would be in an otherwise identical composition lacking said rubusoside, and wherein the concentration of rubusoside is from about 1% to about 40% weight/volume.

30. The composition of claim 29, wherein the organic compound is selected from the group consisting of clofazimine, digoxin, oleandrin, nifedipine, and amiodarone.

31. The composition of claim 29, additionally comprising one or more solubilizing compound to assist in solubilizing the organic compound, wherein said solubilizing compound is selected from the group consisting of mogroside V, cyclodextrin, paeoniflorin, geniposide, steviol monoside, stevioside, and rebaudioside A.

32. The composition of claim 29, additionally comprising one or more pharmaceutical agents selected from the group consisting of complexing agents, cosolvents, surfactants, emulsifiers, liposomes and nanoparticles.

33. A composition comprising an organic compound having low solubility in water, and stevioside; wherein the organic compound is selected from the group consisting of phenazines and riminophenazines; and wherein the concentration of said stevioside in the composition is sufficient to increase the solubility of said organic compound in water by a factor of 2 or more above what the solubility would be in an otherwise identical composition lacking said stevioside, and wherein the concentration of stevioside is from about 1% to about 40% weight/volume.

34. The composition of claim 33, wherein the organic compound is selected from the group consisting of clofazimine, oleandrin, and nifedipine.

35. The composition of claim 33, additionally comprising one or more solubilizing compound to assist in solubilizing the organic compound, wherein said solubilizing compound is selected from the group consisting of mogroside V, cyclodextrin, paeoniflorin, geniposide, steviol monoside, rubusoside, and rebaudioside A.

36. The composition of claim 33, additionally comprising one or more pharmaceutical agents selected from the group consisting of complexing agents, cosolvents, surfactants, emulsifiers, liposomes and nanoparticles.

37. A composition comprising an organic compound having low solubility in water, and rebaudioside A; wherein the organic compound is selected from the group consisting of phenazines, dihydropyridines, amiodarones, and riminophenazines; and wherein the concentration of said rebaudioside A in the composition is sufficient to increase the solubility of said organic compound in water by a factor of 2 or more above what the solubility would be in an otherwise identical composition lacking said rebaudioside A, and wherein the concentration of rebaudioside A is from about 1% to about 40% weight/volume.

38. The composition of claim 37, wherein the organic compound is selected from the group consisting of clofazimine, oleandrin, nifedipine, and amiodarone.

39. The composition of claim 37, additionally comprising one or more solubilizing compound to assist in solubilizing the organic compound, wherein said solubilizing compound is selected from the group consisting of mogroside V, cyclodextrin, paeoniflorin, geniposide, steviol monoside, stevioside, and rubusoside.

40. The composition of claim 37, additionally comprising one or more pharmaceutical agents selected from the group consisting of complexing agents, cosolvents, surfactants, emulsifiers, liposomes and nanoparticles.

* * * * *